United States Patent
Hiraoka et al.

(12) 
(10) Patent No.: US 6,541,217 B2
(45) Date of Patent: Apr. 1, 2003

(54) HEMATOPOIETIC STEM CELL GROWTH FACTOR (SCGF)

(75) Inventors: Atsunobu Hiraoka, 27-34, Kitachuin-cho, Saganisonin-monzen, Ukyo-ku, Kyoto-shi, Kyoto 616-8428 (JP); Atsushi Sugimura, Hokkaido (JP); Hiroyuki Mio, Shizuoka (JP)

(73) Assignees: Kyowa Hakko Kogyo Co., Ltd., Tokyo (JP); Atsunobu Hiraoka, Kyoto (JP)

( * ) Notice: Subject to any disclaimer, the term of this patent is extended or adjusted under 35 U.S.C. 154(b) by 0 days.

(21) Appl. No.: 09/065,040

(22) PCT Filed: Aug. 27, 1997

(86) PCT No.: PCT/JP97/02985

§ 371 (c)(1),
(2), (4) Date: Apr. 27, 1998

(87) PCT Pub. No.: WO98/08869

PCT Pub. Date: Mar. 5, 1998

(65) Prior Publication Data

US 2002/0099196 A1 Jul. 25, 2002

(30) Foreign Application Priority Data

Aug. 27, 1996 (JP) .............................. 8-262252
Mar. 24, 1997 (JP) .............................. 9-087242
Jul. 7, 1997 (JP) ................................. PCT/JP99/2349

(51) Int. Cl.$^7$ ...................... A61K 38/10; C07K 14/475; C12N 1/21; C12N 15/12; C12N 15/63

(52) U.S. Cl. ................ 435/69.1; 435/69.4; 435/69.5; 435/320.1; 435/325; 435/252.3; 435/254.11; 530/350; 530/351; 530/399; 530/387.1; 530/387.9; 574/2; 574/12

(58) Field of Search ................. 530/350, 351, 530/399, 387.1, 387.9; 536/23.1, 23.5; 435/69.1, 69.4, 69.5, 320.1, 252.3, 325, 254.11; 514/12, 2

(56) References Cited

U.S. PATENT DOCUMENTS 5,194,596 A * 3/1993 Tischer et al.
5,200,327 A * 4/1993 Garvin et al. .............. 435/69.5
5,350,836 A * 9/1994 Kopchick et al.
5,358,707 A * 10/1994 Reichert et al. ............ 424/85.1
5,891,429 A * 4/1999 Clark et al. ................. 424/85.1

FOREIGN PATENT DOCUMENTS

EP 0286200 A2 10/1988

OTHER PUBLICATIONS

Benjamin et al., 1998, Development 125:1591–1598.*
Vukicevic et al., 1996, PNAS USA 93:9021–9026.*
Massague, 1987, Cell 49:437–438.*
Pilbeam et al., 1993, Bone 14:717–720.*
Skolnick et al., 2000, Trends in Biotech. 18:34–39.*
Bork, 2000, Genome Research 10:398–400.*
Doerks et al., 1998, Trends in Genetics 14:248–250.*
Smith et al., 1997, Nature Biotechnology 15:1222–1223.*
Brenner, 1999, Trends in Genetics 15:132–133.*
Bork, 1998, Trends in Genetics 12:425–427.*
Hiraoka et al., "Monoclonal Antibodies Against Human Hematopoietic Survival and Growth Factor," *Biomedica Biochimica Acta*, 46(5):419–427 (1987).
Mio et al., "Isolation and Characterization of a cDNA for Human, Mouse and Rat Full–Length Stem Cell Growth Factor, A New Member of C–Type Lectin Superfamily," *Biochemical and Biophysical Research Communications*, 249(1):124–130 (1998).
Hiraoka, A., et al., "Human Hematopoietic Survival and Growth Factor," *Cell Biology International Reports*, vol. 10, No. 5, May 1986, pp. 347–355.
Hiraoka, A., et al., "Cloning, Expression, and Characterization of a cDNA Encoding a Novel Human Growth Factor for Primitive Hematopoietic Progenitor Cells," *Proc. Natl. Acad. Sci. USA*, vol. 94, Jul. 1997, pp. 7577–7582.
Hiraoka, A., et al., "Production of Human Hematopoietic Survival and Growth Factor by a Myeloid Leukemia Cell Line (KPB–M15) and Placenta as Detected by a Monoclonal Antibody," *Cancer Research 47*, Oct. 1987, pp. 5025–5030.
Seed, An LFA–3 cDNA Encodes a Phospholipid–linked Membrane Protein Homologous to its Receptor CD2, *Nature* 329: 840–42 (1987).

* cited by examiner

*Primary Examiner*—Elizabeth Kemmerer
(74) *Attorney, Agent, or Firm*—Finnegan, Henderson, Farabow, Garrett & Dunner, L.L.P.

(57) ABSTRACT

The present invention provides a novel polypeptide possessing growth activities on hematopoietic stem cells, a gene encoding the polypeptide and an antibody reacting specifically with the polypeptide, as well as a method for isolating the above gene and a vector for use in the method. According to the present invention, it is possible to elucidate the pathogenesis of various hematopoietic diseases due to abnormalities in hematopoietic stem cells and of bone marrow inhibition, and to diagnose and treat such diseases. According to the present invention, it is also possible to amplify hematopoietic stem cells in vitro for bone marrow transplantation necessary for the treatment of such diseases or improve efficiency of a gene transfer into hematopoietic stem cells for utilizing the gene therapy. The vector and the method of gene isolation developed to isolate the SCGF gene of the invention are applicable to search for other novel genes and able to contribute to the technological progress in genetic engineering.

33 Claims, 18 Drawing Sheets

HEMATOPOIETIC STEM CELL GROWTH FACTOR (SCGF)

This application is a 371 of PCT/JP97/02985, filed Aug. 27, 1997.

TECHNICAL FIELD OF THE INVENTION

The present invention relates to a novel hematopoietic growth factor protein termed hematopoietic stem cell growth factor (hereinafter referred to as "SCGF") which acts on hematopoietic stem cells to maintain their survival and to induce their proliferation and differentiation. The present invention also relates to a gene coding for SCGF; a vector comprising the gene; a transformant transformed with the vector; a method for producing SCGF; and a method for separating and purifying SCGF. The present invention further relates to the use of SCGF as a therapeutic for hematopoietic insufficiency derived from irradiation or chemotherapy for patients with various hematopoietic diseases or cancers; or the use of SCGF as a reagent for diagnostic analysis. The present invention also relates to the use of SCGF in bone marrow transplantation for the purpose of hematopoietic recovery, for which hematopoietic stem cells can be amplified with SCGF in vitro in a small amount of bone marrow aspirates; and the use of SCGF in gene therapy to improve the efficiency of a gene transfer into hematopoietic stem cells. The invention also relates to a vector developed to isolate the SCGF gene, as well as a method for isolating the gene. The vector and the method can provide promising tools to search for other novel genes for unknown proteins.

TECHNICAL BACKGROUND OF THE INVENTION

Hematopoiesis in the bone marrow is regulated by direct interaction between (i) self-renewable hematopoietic stem cells, hematopoietic progenitor cells derived therefrom and committed to respective differentiation pathways and cell populations at consecutive differentiation stages between the above two types of cells, and (ii) stromal cells as hematopoietic inductive microenvironment supporting the above cells, or by indirect interaction between (i) cells and hematopoietic humoral factors secreted by (ii) cells. A number of hematopoietic humoral factors are also secreted by extramedullary organs such as the kidney or the liver. Peripheral blood cells with a limited life span are continuously recruited through the hematopoietic network spreading over the whole body which results in maintaining the hamarological stasis. The complicated hematopoietic mechanisms have been analyzed using the following two approaches; first, the process of hematopoietic recovery from myelosuppression is studied in vivo in the experimental animals such as mouse, dog or sheep, which are irradiated or given cytotoxic reagents such as 5-fluorouracil. Second, interaction between hematopoietic stem cells and stromal cells or humoral factors is studied in vitro, using a clonal culture of the human and mammalian bone marrow cells.

With the progress in molecular biology, a number of genes for cytokines including hematopoietic growth factors have been successfully cloned. Such cytokines include erythropoietin (hereinafter referred to as "Epo"), thrombopoietin, colony stimulating factors such as granulocyte colony-stimulating factor (hereinafter referred to as "G-CSF"), macrophage colony-stimulating factor (hereinafter referred to as "M-CSF"), granulocyte macrophage colony-stimulating factor (hereinafter referred to as "GM-CSF") interleukins such as IL-1, IL-3, IL-4, IL-5, IL-6, IL-9, IL-11 and IL-12 recently identified stem cell factor (SCF) and flk-2/flt3 ligand (Lin et al., Proc. Natl. Acad. Sci. USA 82, 7580–7584, 1985; de Sauvage et al., Nature 369, 533–538, 1994; Nagata et al., EMBO J. 5, 575–581, 1986; Wong et al., Science 235, 1504–1508, 1987; Miyatake et al., EMBO J. 4, 2561–2568, 1985; Clark et al., Nucleic Acids Res. 14, 7897–7914, 1986; Dorssers et al., Gene 55, 115–124, 1987; Yokota et al., Proc. Natl. Acad. Sci. USA 83, 5894–5898, 1986; Campbell et al., Proc. Natl. Acad. Sci. USA 84, 6629–6633, 1987; Yasukawa et al., EMBO J. 6, 2939–2945, 1987; Yang et al., Blood 74, 1880–1884, 1989; Paul et al., Proc. Natl. Acad. Sci. USA 87, 7512–7516, 1990; Wolf et al., J. Immunol, 146, 3074–3081, 1991; Anderson et al., Cell 63, 235–243, 1990; Lyman et al., Cell 75, 1157–1167, 1993). These cytokines have been well characterized biologically and biochemically, and their industrial production has become possible. G-CSF, M-CSF and Epo are used clinically as recombinant preparations for hematopoietic insufficiency derived from irradiation or chemotherapy and anemia associated with renal failure, respectively. However, when hematopoietic insufficiency due to quantitative or qualitative hematopoietic stem cell abnormalities is treated with the recombinant hematopoietic growth factors, peripheral blood counts are only transiently improved. Hematopoietic insufficiency often recurs with cessation of the hematopoietic growth factors. In other words, presently available hematopoietic growth factors have not achieved radical cure of hematopoietic insufficiency due to hematopoietic stem cell abnormalities.

Auto- or allo-graft of bone marrow, peripheral blood and cord blood hematopoietic stem cells are common procedures for hematopoietic insufficiency. On the other hand, hematopoietic stem cells in the bone marrow, peripheral blood or cord blood cells are tried to be the amplified in vitro with hematopoietic growth factors and then transplanted. Among the factors described above, SCF, IL-3, G-CSF and IL-6 play a major role in amplification of hematopoietic stem cells and immature progenitors. These factors are known to exhibit the so-called "synergistic effect", i.e. they induce higher amplification when used in combination than when used alone. Mouse hematopoietic stem cells can be amplified in vitro to 10-fold and progenitor cells to 1000-fold in response to the hematopoietic growth factors. In human, however, an expected amplification effect has not been achieved with the combination of SCF, IL-3, G-CSF and IL-6 that is effective in the mouse system (Bernstein et al., Blood 77, 2316–2321, 1991; Brandt et al., Blood 79, 634–641, 1992; Srour et al., Blood 81, 661–669, 1993). This not only implies that human cells expressing the receptors for the hematopoietic growth factors are different from mouse ones, but strongly suggests the existence of unknown factors involved in human hematopoiesis.

When host cells are transfected or infected, in gene therapy, with a retrovirus vector carrying a normal gene or a gene of interest, the efficiency of gene transfer will be extremely low if the host cells are not in the cell cycle and, as a result, no expression of the gene can be achieved. If a gene is transferred into the short-lived mature blood cells, gene therapy should be repeated many times since the expression of the gene is transient. Therefore, hematopoietic stem cells are a preferable target for gene transfer, for the reason that it is therapeutically excellent to transfer a gene of interest into hematopoietic stem cells once to thereby supply cells expressing the gene permanently. However, since hematopoietic stem cells are usually quiescent in the $G_0$ phase, attempts have been made to enter them into the cell cycle using a combination of hematopoietic growth factors such as SCF, IL-3, G-CSF, IL-6 and so forth. The efficiency of gene-transfer is still as low as 40%, which is the biggest problem in gene therapy (Nolta et al., Hum. Gene Therapy 1, 257–268, 1990; Stoeckert et al., Exp. Hematol. 18, 1164–1170, 1990; Dick et al., Blood 78, 624–634, 1991; Cournoyer et al., Hum. Gene Therapy 2, 203–213, 1991; Hughes et al., J. Clin. Invest. 89, 1817–1824, 1992).

Hiraoka et al. have found a growth activity on human hematopoietic stem cells in the culture supernatant of normal human peripheral blood mononuclear cells and that of undifferentiated myeloid KPB-M15 cells established from the peripheral blood leukocytes of the patient with chronic myelogenouse leukemia in blast crisis, designated the activity "hematopoietic stem cell growth factor" (SCGF) and tried to purify the factor (Hiraoka et al., Cell Biol. Int. Rep.10, 347–355, 1986; Hiraoka et al., Cancer Res. 47, 5025–5030, 1987). The hematopoietic activities of SCGF include, erythroid burst-promoting activity (hereinafter referred to as "BPA") in the presence of Epo and granulocyte macrophage colony-promoting activity (hereinafter referred to as "GPA") in the presence of GM-CSF on human bone marrow cells, while SCGF lacks colony-stimulating activity (hereinafter referred to as "CSA").

Since human SCGF shows a strict species-specificity, i.e. it is active on human hematopoietic stem or progenitor cells but not on mouse cells, investigators should not use mouse bone marrow cells but human cells for purification and identification of SCGF. Human bone marrow cells are least available due to the limited number of donors, so the progress in the studies is limited and it has been remained ambiguous whether SCGF is different from or identical with a known factor.

PROBLEM FOR SOLUTION BY THE INVENTION

It is an object of the invention to identify the molecular characteristics of the novel hematopoietic growth factor "SCGF" through purification of SCGF protein and cloning of a gene coding for SCGF, and to provide the recombinant SCGF preparation. The present invention intends to contribute to the in vitro amplification of human hematopoietic stem and progenitor cells, amelioration of various hematopoietic disorders, gene therapy and the diagnosis of diseases. In view of the species-specificity of SCGF, the present invention intends to make clear an important aspect of SCGF-concerned hematopoietic mechanisms unidentified expanded from the studies using mouse bone marrrow cells.

Disclosure of the Invention

Since recombinant DNA technology has remarkably advanced, isolation and identification of a gene has become possible even for quite a small amount of a physiologically active protein (Huynh et al., *DNA Cloning I, A Practical Approach*, Glover (ed.), Oxford, Wash., IRL Press, 49–78, 1985; Sambrook, Fritsch and Maniatis, 1989, *Molecular Cloning, A Laboratory Manual*, 2nd Edition, Cold Springs Harbor Laboratory Press, 1989). There are two major methods for isolating a gene. First is a protein-purification leading method, to determination of the partial amino acid sequence; an oprimal oligo-DNA probe is prepared based on the amino acid sequence, then a relevant gene is screened to hybridize with the DNA probe (i.e., a gene which is expected to encode the same amino acid sequence as that of the purified protein), from a large-scale cDNA library. Second is an expression cloning method; a protein is secreted by cells expressing a relevant cDNA clone and detected using an activity assay system or a specific antibody. The latter is superior to the former in that the protein need not be highly purified for isolation of the gene. It means the expression cloning method requires the specific antibody or sensitive activity assay system for successful gene isolation.

The present inventors have modified and improved the expression cloning method. First, the genes totally different from that for SCGF have been tried to be excluded from a cDNA library. Briefly, the positive DNA probes was prepared from DNA of SCGF-producing KPB-M15 cells subtracted with SCGF-infertile MOLT-4 cells, and the negative probe from DNA of the MOLT-4 cells. For a differential cloning, the genes that hybridize with the positive probe but not with the negative probe were sorted from a cDNA library of KPB-M15 cells. Somewhat less sensitive assay system for SCGF activity can be appropriate to detect SCGF cDNA clone by reducing the number of expression samples from the sorted cDNA clones. While a cDNA should be ligated to a phage vector for differential hybridization, it be ligated to a plasmid vector for expression of the cDNA in mammalian cells to rest the SCGF activity of the protein. In order to meet the demand, the inventors have developed a novel vector convertible from a phage vector to a plasmid one on the same vector. Briefly, genes for replication in *E. coli* and expression in mammalian cells were ligated into a λ phage vector with a flanking replication initiator and terminator. The λ phage vector was packaged and coinfected with a helper phage into *E. coli*, replicating to circularize the region between the initiator and terminator. The replicated circular DNA was covered with the coat protein to develop an infectious phagemid. When *E. coli* was infected with, the phagemid, the circular DNA in the phagemid was transferred into the *E. coli*, resulting in transformation of *E. coli*. The DNA between replication initiator and terminator in the λ phage vector was consequently transferred into *E. coli* to be plasmid-like. Since the plasmid-like circular DNA had the ability to replicate in *E. coli* and to be expressed in mammalian cells, the initial λ phage vector had been converted to a plasmid vector without DNA recombination.

A KPB-M15 cDNA library was prepared into the above vector. About 60,000 cDNA clones were sorted to about 6,800 through differential cloning. Gene products expressed in COS cells were screened for BPA. cDNA clone No. 116-10C was isolated as that for SCGF. Nucleotide sequencing showed that the cDNA had 1,196 nucleotides with a long open reading frame that encoded a 245-amino acid polypeptide. About 20 amino acids at an N-terminal region were hydrophobic. No homology with the database in the EMBL and GenBank was found for the cDNA sequence in the total or most of the coding region, though only one short DNA fragment showed partially high homology with the 3' untranslated region of the cDNA clone No. 116-10C. Furthermore, no homology with database in the Swiss-Prot was found for the amino acid sequence. Collectively, cDNA clone No. 116-10C has been confirmed to be a gene coding for the novel hematopoietic growth factor SCGF. Thus, the present invention has been achieved.

Hereinbelow, the present invention will be described in detail.

First, the invention relates to a mammalian polypeptide with BPA or GPA on the bone marrow cells.

Secondly, the invention relates to a mammalian gene that encodes a polypeptide with BPA or GPA on the bone marrow cells.

Thirdly, the invention relates to a vector carrying the above gene.

Fourthly, the invention relates to a transformant transformed with the above vector.

Fifthly, the invention relates to a specific antibody for the above polypeptide.

Sixthly, the invention relates to microorganisms, animal cells or animals producing the above antibody.

Seventhly, the invention relates to a method for producing the above polypeptide by the culture cells possessing the above gene.

Eighthly, the invention relates to a method for purification of the above polypeptide using one or more of an anion exchange, a hydrophobic, a gel filtration, a pigment and lectin affinity, and a metal-chelating chromatography.

Ninthly, the invention relates to a pharmaceutical composition the above polypeptide as an active ingredient.

Tenthly, the invention relates to a λ phage vector which has at least 2 functional DNA regions for replication in *E. coli* and for expression in mammalian cells with a flanking replication initiator and a terminator from a filamentous phage.

Eleventhly, the invention relates to a method for isolating a gene using the above λ phage vector.

(1) The Polypeptide of the Invention (the 1st Invention)

The polypeptide of the invention is that of a mammalian origin possessing BPA or GPA on the bone marrow cells.

BPA can be detected by erythroid bursts formation in a soft agar culture of the bone marrow cells in response to Epo and the polypeptide to be tested. For example, bone marrow cells are seeded at a density of $5 \times 10^4$ /ml into 0.3% agar medium, containing 1 unit/ml of Epo and the polypeptide. Erythroid bursts consisting of erythroblasts are enumerated under an inverted microscope after 14-day culture. GPA can be detected by an increase in the number of GM colonies formed in a soft agar culture of the bone marrow cells in response to GM-CSF and the polypeptide. For example, bone marrow cells are seeded at a density $5 \times 10^4$ /ml in 0.3% agar medium, containing 5 ng/ml of GM-CSF and the polypeptide. GM colonies consisting of granulocytes and macrophages are enumerated under an inverted microscope after 10-day culture. Bone marrow cells are aspirated from the mammalian sternum or ilium, and suspended in a medium, e.g. Iscove's modified Dulbecco's medium (IMDM) containing 10% fetal calf serum (FCS). Low density mononuclear cells are separated by centrifugation on a high density isotonic cushion, e.g. Ficoll.

The polypeptide of the invention can be obtained by the cultures of cells possessing the gene of the invention (the 2nd invention) described below.

Human placenta and KPB-M15 cells are candidates of cells possessing the gene of the invention. Cells with the recombinant gene of the invention are another sources.

Structure of the purified polypeptide of the invention can be analyzed by conventional methods used in protein chemistry, e.g. the method described in Hisashi Hirano, *Structural Analysis of Proteins for Gene Cloning*, Tokyo Kagaku Dojin Co., 1993.

In addition to the use as a pharmaceutical composition described below, the polypeptide of the invention can be used for auto- or allograft of bone marrow, peripheral blood and cord blood hematopoietic stem cells. Hematopoietic stem cells in the bone marrow, peripheral blood or cord blood cells are amplified in vitro with the polypeptide of the invention alone or in combination with hematopoietic growth factors such as G-CSF, GM-CSF, SCF, flk-2/flt3 ligand, IL-1, IL-3 and IL-6. Therefore, bone marrow cells need not be aspirated in an operating room, but a small amount of bone cells should be aspirated easily in a short time at an outpatient clinic which will be sufficient for transplantation. The physical burden of a cell donner, the labor of a medical staff, and the medical cost, associated with bone marrow aspiration, can be saved.

Among the polypeptides of the invention, the following 4 polypeptides described below are particularly preferred.

(i) The following polypeptide (a) or (b):
(a) a polypeptide comprising the amino acid sequence shown in SEQ ID NO: 1;
(b) a polypeptide comprising the amino acid sequence shown in SEQ ID NO: 1 with deletion, substitution or addition of one or more amino acids and having BPA or GPA on human bone marrow cells.

(ii) The following polypeptide (a) or (b):
(a) a polypeptide comprising the amino acid sequence shown in SEQ ID NO: 4;
(b) a polypeptide comprising the amino acid sequence shown in SEQ ID NO: 4 with deletion, substitution or addition of one or more amino acids and having BPA or GPA on human bone marrow cells.

(iii) The following polypeptide (a) or (b):
(a) a polypeptide comprising the amino acid sequence shown in SEQ ID NO: 8;
(b) a polypeptide comprising the amino acid sequence shown in SEQ ID NO: 8 with deletion, substitution or addition of one or more amino acids and having BPA or GPA on mouse bone marrow cells.

(iv) The following polypeptide (a) or (b):
(a) a polypeptide comprising the amino acid sequence shown in SEQ ID NO: 12;
(b) a polypeptide comprising the amino acid sequence shown in SEQ ID NO: 12 with deletion, substitution or addition of one or more amino acids and having BPA or GPA on rat bone marrow cells.

The "deletion, substitution or addition" mentioned herein can be generated by conventional techniques at the time of the filing of this application, e.g. site-specific mutagenesis (Zoller et al., Nucleic Acids Res. 10, 6487–6500, 1982).

KPB-M15 cell line capable of producing the polypeptide (i) above has been deposited with the National Institute of Bioscience and Human-Technology, Agency of Industrial Science and Technology, Ministry of International Trade and Industry (1–3, Higashi 1-chome, Tsukuba City, Ibaraki Pref., Japan) under Accession No. FERM BP-5850 (date of deposit: Mar. 5, 1997).

(2) The Gene of the Invention (the 2nd Invention)

The gene of the invention is that of a mammalian origin encoding a polypeptide with BPA or GPA on the bone marrow cells.

BPA and GPA can be detected as described above.

The gene of the invention can be synthesized from mRNA by PCR on the cDNA from mammalian mRNA as a template, using a forward and a reverse primers synthesized based on the nucleotide sequence shown in SEQ ID NO: 2. Specific examples of the mammals to be used in the invention include, but are not limited to, human and mouse. Specific examples of the primers for PCR include, but are not limited to, the primer shown in SEQ ID NO: 6 and the primer shown in SEQ ID NO: 7. mRNA preparation, cDNA synthesis and PCR can be carried out by conventional methods.

The gene of the invention will be useful as a template essential for a large scale production of a recombinant mammalian SCGF using recombinant DNA technology. SCGF-producing cells can be identified by in situ or Northern hybridization with a part of the DNA sequence of the gene. The genomic DNA for SCGF can be simiarly isolated and characterized. The present gene of the invention can contribute to the diagnosis of various hematopoietic diseases or elucidation of the pathogenesis by analysis for deletion, mutation, and suppressed or excessive expression of the gene. The present invention is accordingly applicable to gene therapy, e.g. introduction of a delered gene, replacement of a mutated gene with a normal one, suppression of excessive gene expression with an antisense DNA (RNA), and so on.

It is possible to isolate and characterize other mammalian SCGF genes highly homologous with human and mouse ones, using a part of the gene of the invention as a probe. Knock-out and transgenic animals constitutively lacking and expressing SCGF gene respectively, are quite significant in analysis for pathogenesism disease model animals and SCGF-concerned hematopoietic mechanism per se.

Among the genes of the invention, the following 4 genes are particularly preferred.

(i) A gene encoding the following polypeptide (a) or (b):
(a) a polypeptide comprising the amino acid sequence shown in SEQ ID NO: 1;
(b) a polypeptide comprising the amino acid sequence shown in SEQ ID NO: 1 with deletion, substitution or addition of one or more amino acids and having BPA or GPA on human bone marrow cells.

(ii) A gene encoding the following polypeptide (a) or (b):
(a) a polypeptide comprising the amino acid sequence shown in SEQ ID NO: 4;
(b) a polypeptide comprising the amino acid sequence shown in SEQ ID NO: 4 with deletion, substitution or addition of one or more amino acids and having BPA or GPA on human bone marrow cells.

(iii) A gene encoding the following polypeptide (a) or (b):
(a) a polypeptide comprising the amino acid sequence shown in SEQ ID NO: 8;
(b) a polypeptide comprising the amino acid sequence shown in SEQ ID NO: 8 with deletion, substitution or addition of one or more amino acids and having BPA or GPA on mouse bone marrow cells.

(iv) A gene encoding the following polypeptide (a) or (b):
(a) a polypeptide comprising the amino acid sequence shown in SEQ ID NO: 12;
(b) a polypeptide comprising the amino acid sequence shown in SEQ ID NO: 12 with deletion, substitution or addition of one or more amino acids and having BPA or GPA on rat bone marrow cells.

The "deletion, substitution or addition" can be generated by site-specific mutagenesis, as described above.

An *E. coli* carrying the gene described in (i) above (*Escherichia coli* SHDM11610C) has been deposited with the National Institute of Bioscience and Human-Technology, Agency of Industrial Science and Technology, Ministry of International Trade and Industry (1–3, Higashi 1-chome, Tsukuba City, Ibaraki Pref., Japan) under Accession No. FERM BP-5849 (date of deposit: Mar. 4, 1997); an *E. coli* carrying the gene described in (ii) above (*Escherichia coli* HSCGF) has been deposited with the same institute under Accession No. FERM BP-5986 (date of deposit: Jun. 19, 1997); an *E. coli* carrying the gene described in (iii) above (*Escherichia coli* MSCGF) has been deposited with the same institute under Accession No. FERM BP-5987 (date of deposit: Jun. 19, 1997); and an *E. coli* carrying the gene described in (iv) above (*Escherichia coli* RSCGF) has been deposited with the same institute under Accession No. FERM BP-6063 (date of deposit: Aug. 19, 1997).

(3) The Vector of the Invention (the 3rd Invention)

The vector of the invention carries the gene of the invention described above. The vector may have additional DNA region, e.g. a replication initiator and terminator, a selective marker gene(s), a promoter to enhance the expression of the gene of the invention, a poly(A) (polyadenylation) signal, and so forth.

The vector of the invention can be prepared by inserting the gene of the invention into the restriction site of a known vector, such as plasmid, cosmid, phage or virus, digested with an appropriate restriction enzyme. Specific examples of the known vectors to be used in the invention include, but are not limited to, pBR322, PACYC, pUC, PGEM, pBC, pGA, Bluescript, pK21, pRSV, pcD, pGEX, CDM8, SHDM, pBV, pSV, pMT2, pYAC, pWE15, pHEBo, EMBL, Charon, M13, λ zap, λ SHDM, λ gt10 and λ gt11 vectors.

(4) The Transformant of the Invention (the 4th Invention)

The transformant of the invention is transformed with the vector of the invention described above. The transformant of the invention can be from any organism species if transformed with the above vector.

The transformant of the invention can be prepared by transforming an appropriate host with the above vector. *E. coli*, yeast, insect and mammalian cells are candidates of the host to be used in the invention. More specifically, the hosts include, but are not limited to, *E. coli* strains such as HB101, JM109, MC1061, BL21, XL1-Blue, SURE, DH1, DH5; yeast strains such as HIS/LI, HF7c; insect cells such as BmN, Sf cells; and mammalian cells such as CHO, COS, MOP, c127, Jurkat, WOP, HeLa, Namalwa cells. An appropriate method of transformation should be selected depending on the host; the calcium phosphate precipitation or electroporation for *E. coli*; the lithium acetate method, spheroplast fusion or electroporation for yeast; viral infection for insect cells; the calcium phosphate precipitation, protoplast fusion, lipofection, the erythrocyte ghost method, liposome fusion, the DEAE-dextran method, electroporation or viral infection for mammalian cells.

(5) The Antibody of the Invention (the 5th Invention)

The antibody of the invention reacts specifically with the polypeptide of the invention described above. The antibody of the invention can be either a monoclonal or a polyclonal antibody if specifically reactive with the above polypeptide.

The antibody of the invention can be prepared by conventional methods. In vivo method and in vitro method are a single or multiple immunization, at several week interval, with antigen and immunocompetent cells plus adjuvant, respectively. Specific examples of the immunocompetent cells capable of producing the antibody of the invention include spleen, tonsil and lymph node cells. Whole molecule of the polypeptide of the invention need not be necessarily used as an antigen, but a part of the polypeptide may well be antigenic. A short polypeptide, particularly of about 20 amino acids, should be chemically linked to a highly antigenic carrier protein such as Keyhole Lympet hemocyanin or bovine serum albumin. Alternatively, the polypeptide is covalently bound to a branched skelton polypeptide such as lysine-core MAP (Posnett et al., J. Biol. Chem. 263, 1719–1725, 1988; Lu et al., Mol. Immunol. 28, 623–630, 1991; Briand et al., J. Immunol. Methods 156, 255–265, 1992). Complete or incomplete Freund's adjuvant and aluminium hydroxide gel can be used as the adjuvant. Animals to be immunized with the antigen include mouse, rat, rabbit, sheep, goat, chicken, cow, horse, guinea pig and so forth. Blood is obtained from animals immunized, and polyclonal antibody immunoglobulin is purified from serum by ammonium sulfate precipitation, anion exchange, protein A or G chromatography. An antibody can be purified from eggs in the case of immunized chicken. Immunocompetent cells (immunized in vitro or recovered from the immunized animals as described above) are fused with parental cells, giving rise to hybridoma cells. Monoclonal antibody is purified from culture supernatants of the hybridoma cells or ascites of animals transplanted with the hybridoma cells intraperitoneally. Specific examples of the parental cells include X63, NS-1, P3U1, X63.653, SP2/0, Y3, SK0-007, GM1500, UC729-6, HM2.0 and NP4-1 cells. Alternatively, immunocompetent cells (immunized in vitro or recovered from the immunized animals) are infected with appropriate virus such as EB virus, resulting in immortalized, antibody-producing cells, from which monoclonal antibody can be prepared. Genetic engineering can be applied to antibody production. For example, an antibody gene can be amplified by PCR from immunocompetent cells (immunized in vitro or recovered from the immunized animals), and transferred into E. coli to produce the antibody. Alternatively, the antibody can be expressed as a fusion protein on the surface of a phage.

immunoassay for SCGF concentration in patients tissues or organs, using the antibody of the invention, elucidates relationship between SCGF and pathogenesis or clinical course of various diseases. The antibody of the invention is versatile for diagnosis, treatment of diseases and efficient affinity purification of SCGF.

(6) The Antibody-Producing Organism of the Invention (the 6th Invention)

The microorganisms, animal cells or animals of the invention produce the antibody of the invention described above. Specific examples of the microorganisms, animal cells or animals include, but are not limited to, E. coli transformed with the gene encoding the antibody of the invention; a phage expressing the gene for antibody of the invention as a fusion protein on the surface, and the hybridoma cells described above.

(7) Method for Producing the Polypeptide of the Invention (the 7th Invention)

The polypeptide of the invention can be produced by the culture of cells carrying the gene of the invention described above.

There exist two types of cells that express the gene of the invention; human placenta and KPB-M15 cells naturally express the gene, and COS and CHO cells should be transferred with the gene. The polypeptide of the invention can be purified from the culture supernatants of the above cells using purification method of the invention described below. Alternatively, the polypeptide can be extracted from cellular lysates. The cells are broken by physical shearing using a clounce homogenizer or ultrasonication, or lyzed with surfactants such as Triton X-100, Nonidet P-40 and sodium lauryl sulfate (SDS).

(8) Method to Purify the Polypeptide of the Invention (the 8th Invention)

The polypeptide of the invention can be purified using one or more of an anion exchange, a hydrophobic, a gel filtration, a pigment and lectin affinity, and a metal-chelating chromatography.

Crude sample is applied to an anion exchange, for example, DEAE-Sephacel column, washed to let unabsorbed proteins flow-through, and eluted with a linear increasing NaCl gradients. Crude sample is applied to a hydrophobic, for example, Octyl-Sepharose column, and flow-through fractions are collected. Crude sample is fractionated through a gel filtration, for example, Sephacryl S-200 HR column. Crude sample is applied to a pigment affinity, for example, Red- or Blue-Sepharose column, and flow-through and early eluted fractions are collected. Crude sample is applied to a lectin affinity carrier, for example, wheat germ agglutinin (WGA)-agarose or Concanavalin A (ConA)-Sepharose column, and flow-through fractions are collected. Crude sample is applied to a metal-chelating, for example, $Cu^{2+}$-chelating Sepharose column, washed to let unadsorbed molecules flow-through, and eluted with a linear increasing glycine gradients.

(9) The Pharmaceutical Composition of the Invention (the 9th Invention)

The pharmaceutical composition of the invention comprises the polypeptide of the invention as an active ingredient.

The pharmaceutical composition of the invention is administered alone or in combination with other hematopoietic growth factor(s) systemically or locally, and orally or parenterally. The composition is administered at an effective close to ameliorate hematopoietic insufficiency by the hematopoietic activity of SCGF. However, the dosage should be flexible and proper, since the administration dose varies depending on the age, body weight, conditions and reactivity of a patient, route of administration and so on.

For oral administration, the pharmaceutical composition of the invention can be as a solid composition such as tablets, soft and hard capsules, pills, powder and granules, or a liquid composition such as solution, syrup and suspension. For parental administration, the pharmaceutical composition of the invention can be an endermic formulation for external use such as solution, suspension, emulsion, ointment, cream, gel, rosol; a suppository; or an injectable formulation for intravenous, intramuscular or subcutaneous injection.

A pharmaceutically inactive carrier for the pharmaceutical composition can be a diluent such as purified water, lactose, glucose, starch, mannitol, hydroxypropylcellulose, polyvinylpyrrolidone, magnesium aluminate metasilicate, gum-arabic, talc, a vegetable oil or yellow petrolatum. Further, pharmaceutically active additives can be any of conventional, pharmaceutically acceptable materials such as lubricants (magnesium stearate, etc.), disintegrators (fibrin calcium glycolate, etc.), stabilizers (human serum albumin, etc.) and resolution adjuncts (arginine, aspartic acid, etc.).

The solid composition for oral administration can be tablets formulation coated with one or more layers of white sugar, gelatin, hydroxypropyl-cellulose and hydroxypropylmethylcellulose phthalate to be dissolved in the stomach or small intestine. The liquid composition for oral administration can contain purified water, ethanol, solutions, syrups, suspensions, emulsions, elixirs and so on. Further, the composition can contain flavoring agents, preservatives and the like in accordance with appropriate standards for pharmaceutical combination.

The injectable formulation for intravenous, intramuscular or subcutaneous injection can contain, as a pharmaceutically inactive carrier, a diluent such as distilled water for injection, physiological saline, propyrene glycol, polyethylene glycol, a vegetable oil (e.g., olive oil) or an alcohol (e.g., ethanol). In addition, the formulation can contain, as pharmaceutically active additives, preservatives, stabilizers, emulsifiers, buffers, dispersants, resolution adjuncts and the like in accordance with appropriate standards for pharmaceutical combination. The injectable formulations are sterilized by filter-sterilization, addition of a bactericide, or irradiation. Alternatively, a solid composition (such as a lyophilized preparation) can be restored with an aseptic distilled water for injection or the like before administration.

The pharmaceutical composition of the invention is used alone or in combination with other hematopoietic growth factor(s) (such as Epo, G-CSF, GM-CSF and SC) to ameliorate such hematopoietic insufficiency that could not have been improved with known hematopoietic growth factors. Hematopoietic insufficiency to be treated with the pharmaceutical composition of the invention include hematopoietic diseases due to quantitative or qualitative abnormalities in hematopoietic stem cells; aplastic anemia, paroxysmal nocturnal hemoglobinurea, chronic myelocytic leukemia, polycythemia vera, essential thrombocythemia, myelofibrosis, myelodysplastic syndrome and acute leukemia; and hematological diseases such as megaloblastic anemia, AIDS, multiple myeloma, metastatic cancer of the bone marrow, and drug-induced myelosuppression. The pharmaceutical composition of the invention is effective to prevent and ameliorate hematopoietic insufficiency due to irradiation or chemotherapy of the patients with malignant lymphoma or other solid tumors.

The pharmaceutical composition of the invention is applicable to gene therapy; supplementation of a normal gene into enzyme deficiencies (e.g. adenosine deaminase deficiency); replacement of an abnormal gene with a normal gene in genetic mutations (e.g. hemoglobin opathy); and introduction of a gene encoding growth inhibitory factors against cancer cells. Since quiescent hematopoietic ste, cells can enter the cell cycle with the composition of the invention alone or in combination with other hematopoietic growth factor(s) transfection efficiency of a retrovirus vector carrying a normal gene or a gene of interest into those cells is remarkably improved. Once hematopoietic stem cells into which the gene has been introduced are transplanted, they continuously recruit mature blood cells carrying the gene to alleviate or cure the relevant genetic disorders.

(10) The λ Phage Vector of the Invention (the 10th Invention)

The λ phage vector of the invention has at least 2 functional DNA regions for replication in *E. coli* and for expression in mammalian cells with a flanking replication initiator and a terminator from a filamentous phage.

A filamentous phage is a bacteriophage with a single-stranded circular DNA, which specifically infects F fractor-containing *E. coli*. Specific examples of the phage include M13, f1 and fd phages. "A replication initiator" is a nucleotide region which the filamentous phage recognizes to start DNA replication e.g. the nucleotide base sequence of the NheI-DraIII region of M13 phage replication origin gene (ori). "A replication terminator" is a nucleotide region which the filamentous phage recognizes to stop DNA replication, e.g. the nucleotide sequence of the AvaI-RsaI region of M13 phage ori gene. The λ phage vector of the invention should have at least 2 functional DNA regions for replication in *E. coli* and for expression in mammalian cells with a flanking replication initiator and a terminator of a filamentous phage. "A DNA region for replication in *E. coli*" is a replication initiation region (ori) of *E. coli*, e.g. the ColE1 ori. "A DNA region for expression in a mammalian cells" consists of at least a promoter and a poly(A) addition signal for efficient expression of a foreign gene based on DNA from a virus capable of infecting mammalian cells. A virus capable of infecting mammalian cells include SV40 virus, BK virus, papilloma virus, adenovirus, retrovirus, vaccinia virus, EB virus and so forth. A λ phage vector is a vector from bacteriophage λ-derived DNA. Specific examples of λ phage vector include λ SHDM and λ CDM both described in Examples of the present invention, λ gt10, λ gt11, EMBL3, EMBL4 and Charon4A.

The vector of the invention and the method of the invention for isolating a gene described below are applicable to the search for other novel genes, and can contribute to the technical development in novel genes-related the fields of genetic engineering and biotechnology.

(11) The Method of the Invention for Isolating a Gene (the 11th Invention)

The method of the invention for isolating a gene utilizes the λ phage vector of the invention described above. Specifically, a method consisting of the following 4 steps may be illustrated by example, but the method of the invention is not limited to this method.

A) First Step mRNA is prepared from cells producing a protein of interest. cDNA is synthesized from the mRNA, and ligated into the cloning site between the replication initiator and terminator of the λ phage vector of the invention. A host cell is infected with the recombinant phage vector to provide a phage cDNA library. A protein of interest can be, but is not limited to, the polypeptide of the invention (SCGF). Any protein can be used if it has some activity or function assayable for screening. Cells producing a protein of interest can be, but are not limited to, KPB-M15 cells producing SCGF. Alternatively, a protein of interest can be detected with the specific antibody. mRNA can be prepared, and cDNA synthesized using conventional methods. Host cells to be infected can be conventional host cells such as *E. coli*.

B) Second Step

The specific differential phage cDNA library is made of clones that hybridize with a positive probe but not with a negative probe.

The positive probe is single-stranded cDNA (sscDNA) synthesized from the mRNA of the cells producing the protein of interest and subtracted with the mRNA of cells that closely resemble the above cells but do not produce the protein of interest. The negative probe is an sscDNA synthesized from the mRNA of the cells not producing the protein of interest. Differential cloning with the positive and the negative probes exclude the housekeeping cDNA clones irrelevant to the production of the protein of interest, leading to great reduction in the number of cDNA clones for screening. Methods other than differential cloning can be used for that purpose.

C) Third Step

Plasmids are prepared from the above-sorted cDNA clones the λ phage vector of the invention and transfected into a host cells capable of producing the protein of interest. The host cells producing the protein of interest are identified by screening assay for the activity or function or with a specific antibody.

Specific examples of the host cells capable of producing the protein of interest include, but are not limited to, COS-1 cells.

D) Fourth Step

The plasmid is prepared from host cells such as *E. coli*, and then a gene of interest is isolated from the plasmid.

EXAMPLES

Hereinbelow, the present invention will be described in more detail with reference to the following Examples, which should not be construed as limiting the scope of the invention.

Example 1

Preparation of mRNA from KPB-M15 Cells

Total RNA was prepared from KPB-M15 cells known to produce the polypeptide of the invention, according to the method of Chomczynski and Sacchi (Anal. Biochem. 162, 156–159, 1987).

KPB-M15 cells were lyzed in 25 mM sodium citrate buffer containing 4 M guanidine thiocyanate, 0.5% Sarkosyl and 0.1 M 2-mercaptoethanol (2-ME) (Solution D). The lysates were phenol/chloroform-extracted under acidic conditions followed by precipitation of the mRNA in the aqueous phase with 2-propanol.

Oligotex dT30 beads (Takara, Ohtsu) were mixed with the total RNA solution at 37° C. under NaCl of over 0.5 M. After wash, mRNA bound to the beads was dissociated with 10 mM Tris-HCl buffer (pH 7.5) (TE) plus 1 mM EDTA.

Example 2

Synthesis of cDNA from KPB-M15 Cells (KPB-M15 cDNA)

cDNA synthesis was carried out using ZAP-cDNA Synthesis Kit (Stratagene, Calif., La Jolla).

Nucleic acid mixture containing Me-dCTP, a linker primer (FIG. 1) and a reverse transcriptase (RTase) was reacted at 37° C. with mRNA solution from KPB-M15 cells to synthesize the first strand DNA (1st Str). RNAse H and DNA polymerase I (DNApolyI) were reacted at 16° C. with the mixture to synthesize the second strand DNA (2nd Str). The ends of the synthesized cDNA were made blunt with T4 DNA polymerase, ligated to EcoRI adaptor (FIG. 1) at 8° C. with T4 DNA ligase, and phosphorylated with T4 polynucleotide kinase (PNKinase). The cDNA was digested at 37° C. with XhoI, and size-fractionated by BioGel A50m column (BioRad, Calif., Hercules) equilibrated with TE plus 0.1 M NaCl (STE) to collect cDNA of over 500 base pairs (bp).

Example 3

Construction of λ CDM and λ SHDM Vectors

λ CDM and λ SHDM vectors were constructed by insertion of linearized CDMflit and SHDM plasmids, the former of which was produced from CDM8 (Seed, Nature 329, 840–842, 1987), into λ phage vectors, respectively.

λ CDM was constructed as follows; the stuffer XbaI-HindIII region of CDM8 was replaced with a PRC/CMV polylinker (Invitrogen, Calif., San Diego) to develop construct CDMmcs. The EcoRV-EcoRI region in the polylinker was replaced with a pBS (Stratagene) polylinker SmaI-EcoRI fragment, leading to the EcoRV site-eliminated CDMmcs(-v). (SEQ ID NO: 3). The synthetic DNA (SEQ ID NO: 3), which has a part of the overlapping region between the M13 initiator and terminator (FIG. 2) and an EcoRV site at its '5 end, was ligated with the HinfI-RsaI fragment to the DraIII-SacII region of CDMmcs(-v) to develop CDMflit; the EcoRV site was located between M13 initiator and terminator. On the other hand, the λ phage vector of the invention was modified from λ Bluemid (Clontech, Calif., Palo Alto); λ Bluemid was digested with NotI to remove the NotI-NotI fragment, and the left and right arms were ligated. To eliminate, the XhoI site, the NotI-NotI region-deleted fragment was digested with XhoI, blunt-ended with T4 DNA polymerase, and ligated with T4 DNA ligase. The resultant vector was designated λ b-x. The CDMflit was linearized with EcoRV, and ligated to the NotI site of λ b-x to develop A CDM (FIG. 4).

SHDM was constructed aw follows; CDMflit was digested with AatI, where a BamHI linker (CGGATCCG) was ligated to introduce a BamHI site.

The plasmid was digested with BamHI to provide 3 DNA fragments, of which the fragment containing SV40 ori and Py ori was discarded. The remaining 2 fragments were ligated to develop CDMflit(-sv, py). The Py ori cut out from CDMflit with NcoI was blunt-ended with T4 DNA polymerase and then introduced into the NheI site of CDMflit (-sv, py) to develop CDMflit(-sv). CMV promoter was removed from CDMflit(-sv) with NruI and HindIII, and replaced with Hind III—Pvu II SV40 early promoter fragment from pSV2neo (Southern and Berg, J. Mol. Appl. Genet. 1, 327–341, 1982) to develop SDMflit. A synthetic DNA of about 300 bp corresponding to the R region and a part of the U5 region of HTLV-1 LTR was introduced into the HindIII site of SDMflit to develop SHDMflit. A fragment of SV40 16S splicing sequence was prepared from pL2 with XhoI-BanIII, and introduced into the SpeI site of SHDMflit to develop SHDM (FIG. 3). SHDM was linearized with EcoRV and ligated to the NotI site of λ b-x to develop λ SHDM (FIG. 4).

Epo cDNA was inserted into λ SHDM and λ CDM vectors by the methods described in Examples 4 to 7 and expressed in COS-1 cells. λ SHDM-bearing cells yielded in higher Epo production by 25% than other vector-bearing cells. Consequently, the inventors decided to use λ SHDM in the following Examples.

Example 4

Insertion of KPB-M15 Cell-Derived cDNA into λ SHDM Vector

λ SHDM vector was digested with XhoI and EcoRI to form a cDNA insertion site. The vector arms were fractionated from the XhoI-EcoRI fragment through a BioGel A50m column equilibrated with STE. The vector arms were dephosphorylated with calf intestine alkaline phosphatase (CIAP). The KPB-M15 cDNA from Example 2 above was ligated with T4 DNA ligase to the XhoI-EcoRI-digested, dephosphorylated λ SHDM vector.

Example 5

Phage Packaging of the KPB-M15 cDNA-bearing λ SHDM Vector

The cDNA-bearing vector in Example 4 was phage-packaged, using the freeze-thawed extract and the sonicated extract of Gigapack-Gold Packaging Extract Kit (Stratagene), and modulated with 50 mM Tris-HCl storage solution (SM) containing 0.1 M NaCl, 8 mM magnesium chloride ($MgCl_2$) and 0.01% gelatin, and a small amount of chloroform to provide a phage cDNA library (hereinafter referred to as "λ SHDM (KPB) phage"). SURE E. coli in 10 mM magnesium sulfate ($MgSO_4$) was infected with λ SHDM (KPB) phage, temperature melting agarose in mixed with NZYM (0.5% NaCl, 0.5% yeast extract, 0.2% $MgSO_4$ and 1% NZ amine), and seeded onto Luria-Bertani (LB medium; 0.5% NaCl, 1% bacto-tryptone and 0.5% yeast extract) agar plates. Plaques were counted after overnight culture; $1.67 \times 10^6$ pfu for the total λ SHDM (KPB) phage.

The phage clones randomly selected from each plaque were coinfected with a quite small amount of helper phage R408 into XL1-Blue E. coli in 10 mM $MgSO_4$ to develop a phagemid. The phagemid was infected into MC1061/P3/PCJ E. coli in NZYM, and cultured overnight on ampicillin (Amp) and tetracycline (TC) selective LB agar plates to form pSHDM (KPB) plasmid-carrying E. coli colonies. Plasmid DNA was prepared from Amp/TC-resistant colonies by alkaline lysis procedure (Birnboim and Doly, Nucleic Acids Res. 7, 1513–1523, 1979; Ish-Horowicz and Burke, Nucleic Acids Res. 9, 2989–2998, 1981), and digested with XhoI and EcoRI. A 500 bp-3 kb KPB-M15 cDNA was inserted in about 70% of the clones, as detected by agarose gel electrophoresis.

Example 6

Construction of a Differential cDNA Library

λ SHDM (KPB) phage in Example 5 was transferred onto duplicate nitrocellulose filters, lysed with alkali, neutralized and heated at 80° C. for about 2 hours. The phage DNA fixed on each filter was hybridized with $^{32}$P-labelled positive and negative probes, washed to remove unbound probes, and subjected to autoradiography. The clones both positive for the positive probe and negative for the negative probe were selected as the KPB-M15-specific differential phage library.

The KPB-M15-specific positive probe was prepared from KPB-M15 cDNA by subtraction; the KPB-M15 cDNA which hybridize with mRNA from SCGF-infertile MOLT-4 cells was excluded as genes common in both cells, and the remaining cDNA was the positive probe.

More specifically, 1st Str cDNA was synthesized from KPB-M15 mRNA (as described in Example 1) using an oligo(dT) primer and SuperScript™ R Tase (GIBCO-BRL, N.Y., Grand Island). KPB-M15 sscDNA was fractionated from the template mRNA hydrolyzed with alkali through a Sephadex G-50 (Pharmacia, Sweden, Uppsala) column equilibrated with STE, and annealed with an excess of MOLT-4 mRNA at 65° C. for over 40 hours. The reaction mixture was applied to a hydroxyapatite (BioRad) column equilibrated with 0.12 M sodium phosphate buffer (pH 6.5); flow-through fractions were collected, and after alkali treatment, fractionated through Sephadex G-50 gel filtration. Fractions around the void volume were collected as the positive probe. MOLT-4 mRNA was prepared from total RNA as described in Example 1; MOLT-4 total RNA was applied to an oligo(dT) cellulose column equilibrated with 10 mM Tris-HCl buffer (pH 7.5) containing 0.5 M potassium chloride (KCl), and bound mRNA was eluted with 10 mM Tris-HCl buffer (pH 7.5).

sscDNA was synthesized, as described above, from MOLT-4 mRNA as described in Example 1, and used as the negative probe.

The probes were labelled using Multilabelling Kit (Amersham, England, Buckinghamshire, Amersham); the KPB-M15 specific sscDNA or the MOLT-4 sscDNA was heated at 95° C., cooled rapidly on ice, and mixed with random primers, $^{32}$P-labelled dCTP and Klenow enzyme to synthesize $^{32}$P-labelled probes. Unreacted $^{32}$P-labelled dCTP was removed using a Sephadex G-50 column equilibrated with STE.

Example 7
Expression Cloning of SCGF cDNA

Clones of pSHDM(KPB)-carrying *E. coli* prepared in Example 6 were individually cultured for each 48 clones to make up into a pool. Crude plasmid DNA was prepared from each pool by alkaline lysis procedure. Purified mix plasmid cDNA was purified by quillibrium centrifugation in cesium chloride-ethidium bromide gradients.

COS-1 cells (Accession No. ATCC CRL-1650; SV40-transformed fibroblastoid cell line from a simian kidney, were transfected at 37° C. under 5% $CO_2$ in air with 3.3 μg/ml plasmid cDNA in Dulbecco's modified Eagle medium (DMEM, Nissui, Tokyo) containing 100 μg/ml DEAE-dextran and 100 μM chloroquine (a transfection medium). The cells were incubated in DMEM-10% FCS containing 10% dimethylsulfoxide (DMSO), and then cultured overnight in DMEM-10% FCS. Another cycle of transfection, i.e. double transfection was followed by 3- to 5- day cultures in serum-free DMEM. The COS-1 culture supernatants were concentrated as follows; they were diluted with over 7 volumes of 20 mM HEPES buffer (pH 6.0) containing 0.01% Tween 80, applied to a DEAE-Sephacel (Pharmacia) column equilibrated with 20 mM HEPES buffer (pH 6.0) containing 20 mM NaCl and 0.01% Tween 80, washed thoroughly with the same butter, and eluted with 20 mM HEPES buffer (pH 6.0) containing 0.25 M NaCl and 0.01% Tween 80.

The concentrated COS-1 culture supernatants were screened for BPA. BPA on human bone marrow cells was assayed as follows; human bone marrow cells (2.5 mp) were aspirated from the sternum of healthy adult volunteer after obtaining informed consent. Low density mononuclear cells were separated with Ficoll Pack (Pharmacia), washed with IMDM (GIBCO) 3 times, suspended in IMDM-10% FCS (CSL, Australia, Melbourne) 10 ml and incubated at 37 ° C. for 75 minutes. Non-adherent cells ($5 \times 10^4$ /ml) were cultured in IMDM containing the COS-1 culture supernatants, 1 unit/ml recombinant human Epo (Espo; Kirin-Sankyo, Tokyo), 20% FCS, $5 \times 10^{-5}$ M 2-ME and 0.3% Bacto-agar. After 14-day culture, erythroid bursts were enumerated under an inverted microscope.

Pool Nos. 71, 86, 116 and 130 showed relatively high BPA at the initial screening for 137 pools. A single plasmid cDNA was prepared from the clones in each selected pool, and transfected into COS-1 cells again. The clone No. 116-10C was highly positive for BPA at the secondary screening. Sequencing on 373ADA autosequencer (Perkin-Elmer Applied Biosystems, Conn., Norfolk), indicated that the clone No. 116-10C had cDNA with the nucleotide sequence shown in SEQ ID NO: 2. No homology with the databases in the EMBL and GenBank (Lipman and Pearson, Science 227, 1435–1441, 1985) was found for the cDNA sequence in the total or most of the coding region, though only one short DNA fragment showed partially high homology with the 3' untranslated region of the cDNA clone No. 116-10c. A long open reading frame encoded a 245-amino acid polypeptide with about 20 hydrophobic amino acids at an N-terminal region (Hopp and Wood, Proc. Natl. Acad. Sci. USA 78, 3824–3828, 1981) as shown in SEQ ID NO: 1. No homology with the database in the Swiss-Prot was found for the amino acid sequence.

Example 8
Assay for the Hematopoietic Activity in the Culture Supernatant of SCGF cDNA Clone No. 116-10C-Expressing COS-1 Cells COS-1 cells were transfected with 1.3, μg/ml clone No. 116-10c plasmid cDNA as described in Example 7.

BPA of the culture supernatant was assayed as described in Example 7. GPA was assayed as follows; human bone marrow cells ($5 \times 10^4$/ml) prepared in Example 7 were cultured in IMDM containing the COS-1 culture supernatants, 5 ng/ml recombinant human GM-CSF (Genzyme, Mass., Cambridge), 20% FCS, $5 \times 10^5$ 2-ME and 0.3% Bacto-agar. After 10-day culture, GM colonies consisting of granulocytes and macrophages were enumerated under an inverted microscope. Dose-dependent BPA and GPA were observed (FIG. 5).

Example 9
Assay for of the Hematopoietic Activity in the Serum-Free Culture Supernatant of KPB-M15 Cells KPB-M15 cells ($1-2 \times 10^6$ /ml) grown in RPMI-1640 (GIBCO)-10% FCS were transferred to the serum-free culture for 3–4 days. BPA and GPA of the culture supernatants were assayed as described in Examples 7 and 8, respectively. Dose-dependent BPA and GPA were observed (FIG. 6). On the other hand, little activity was seen in the culture supernatants of K562 and MOLT-4 cells prepared under the same conditions.

Example 10
Preparation of an Anti-SCGF Polyclonal Antibody

The pGEX-2T vector (Pharmacia; FIG. 7) was digested with NotI, blunt-ended with T4 DNA polymerase, and by digested with BamHI to form an insertion site. NcoI-BamHI linker (FIG. 7) and 116-10C NcoI-XbaI DNA fragment were ligated to the vector with T4 DNA ligase to develop circular pGEX-2T(116-10C). The pSHDM(116-10C) plasmid cDNA was digested with XbaI, blunt-ended with T4 DNA polymerase, and digested with NcoI to develop 116-10c NcoI-XbaI DNA fragment. JM109 E. coli was transformed with PGEX-2T (116-10C), and induced with isopropyl β-D-thiogalactoside (IPTG) to produce glutathione S-transferease/116-10C fusion protein (GST/116-10C). The inclusion body was lyzed with urea, and the GST/116-10C fusion protein was affinity purified through a glutathione-Sepharose (Pharmacia) column. The fusion protein was digested with thrombin, and 116-10C protein was purified through a MonoQ (Pharmacia) column. Rabbits were immunized with the 116-10C SCGF protein and Freund's complete adjuvant (DIFCO, Mich., Detroit) 3 times at 2-week intervals. Anti-serum was harvested 2 weeks after the final boost and the antibody was purified through a protein A-Sepharose (Pharmacia) column. The polyclonal antibody was confirmed to react with 116-10C protein by enzyme-linked immunosorbent assay (ELISA).

Example 11
Preparation of an Anti-SCGF Monoclonal Antibody

A monoclonal antibody was prepared according to the method of Oi and Herzenberg (*Selected Methods in Cellular Immunology*, Misheli and Shiigi (eds.), San Francisco, WH Freeman Publishing, pp. 351–372, 1981). Briefly, BALB/C mice were immunized twice at 3-week interval with any of 116-10C protein as described in Example 10, a partially purified SCGF from culture supernatants of mitogen-stimulated human peripheral blood mononuclear cell, or a partially purified SCGF as described in Example 20 and Freund's complete adjuvant. Spleen cells were harvested 3 days after the final boost, and mixed at the same ratio with a mouse myeloma cell line P3X63-Ag8.653 ($1.5 \times 10^8$) (Koehler and Milstein, Nature 256, 495–497, 1975). They were fused with 50% polyethylene glycol 4,000. Hybridoma cells were selected in HAT medium (hypoxanthine, aminopterin and thymidine) up to day 11, fed with thymocytes on day 23, and then transferred to HT medium (hypoxanthine and thymidine). Two weeks thereafter, the hybridoma cells were cloned on the thymocyte feeder by limiting dilution. The cloned anti-SCGF antibody-producing hybridoma cells were administered intraperitoneally to BALB/c mice pre-treated with pristane (0.5 ml/mouse), and ascites were harvested about 2 weeks afterwards. The antibody was purified from culture supernatants of the hybridoma cells or ascites through a protein G-Sepharose column. The antibody was confirmed to react with SCGF by ELISA. The effect of this purified anti-SCGF monoclonal antibody on SCGF activity was tested; serially diluted antibodies were added to partially purified SCGF, and incubated at 37° C. for 2 hours and then at 4° C. overnight. The monoclonal antibody specifically neutralized BPA and GPA of SCGF (FIG. 8).

Example 12
Purification of SCGF through DEAE-Sephacel

The culture supernatants of KPB-M15 cells as described in Example 9 was mixed with 6.5 volumes of 20 mM phosphate buffer (pH 6.0) and 1/100 volume of 1% Tween 80 to adjust salt concentration and pH. It was applied to a DEAE-Sephacel column equilibrated with 20 mM phosphate buffer (pH 6.0) containing 20 mM NaCl and 0.01% Tween 80 (all the buffers used in the following purification of SCGF contained 0.01% Tween 80), washed thoroughly with the same buffer, and eluted with a linear NaCl gradient (0.02–0.5 M). Salt concentration was adapted to be physiological through a PD-10 column equilibrated with 20 mM phosphate buffer (pH 7.4) containing 0.15 M NaCl. BPA in each fraction was assayed as described in Example 7. BPA was found in fractions eluted at about 0.1 M NaCl (FIG. 9).

Example 13
Purification of SCGF through Octyl-Sepharose

The culture supernatants of KPB-M15 cells as described in Example 9 was mixed with 2.56 g of NaCl and 1% Tween 80 to adjust the concentrations to 4M and 0.01%, respectively. It was applied to an octyl-Sepharose CL-4B (Pharmacia) column equilibrated with 20 mM phosphate buffer (pH 7.4) containing 4M NaCl, washed thoroughly with the same buffer, and eluted with a linear NaCl gradient (4–0.02 M). BPA in each fraction was assayed as described in Example 12. BPA was found in passing through fractions (FIG. 10).

Example 14
Purification of SCGF through $Cu^{2+}$ Chelating-Sepharose

The culture supernatants of KPB-M15 cells as described in Example 9 was dialyzed against 10 mM phosphate buffer (pH 7.4) containing 0.5 M NaCl. It was applied to a $Cu^{2+}$ chelating-Sepharose CL-4B (Pharmacia) column equilibrated with the same buffer, washed thoroughly with the same buffer, and eluted with a linear glycine gradient (0–0.1 M). BPA in each fraction was assayed as described in Example 12. BPA was found in fractions eluted at about 35 mM glycine (FIG. 11).

Example 15
Purification of SCGF through ConA-Sepharose

The culture supernatant of KPB-M15 cells as described in Example 9 was dialyzed against 20 mM Tris-HCl buffer (pH 7.4) containing 0.15 M NaCl. It was applied to a ConA-Sepharose CL-4B (Pharmacia) column equilibrated with the same buffer, washed thoroughly with the same buffer, and eluted with a linear α-methylmannose gadient (0–0.5 M). BPA in each fraction was assayed as described in Example 12. BPA was found in flow-through fractions (FIG. 12).

Example 16
Purification of SCGF through WGA Agarose

The culture supernatants of KPB-M15 cells as described in Example 9 was dialyzed against 10 mM phosphate buffer (pH 7.4) containing 0.15 M NaCl. It was applied to a WGA-agarose (Seikagaku Corp., Tokyo) column equilibrated with the same buffer, washed thoroughly with the same buffer, and eluted with a linear N-acetylglucosamine gradient (0–0.2 M). The fractions were dialyzed against IMDM containing 0.01% Tween, and BPA in each fraction was assayed as described in Example 7. BPA was found in flow-through fractions (FIG. 13).

Example 17
Purification of SCGF through Blue-Sepharose

The culture supernatant of KPB-M15 cells as described in Example 9 was dialyzed against 50 mM Tris-HCl buffer (pH 7.0) containing 50 mM NaCl. It was applied to a Blue-Sepharose CL-6B (Pharmacia) column equilibrated with the same buffer, washed thoroughly with the same buffer, and eluted with a linear NaCl gradient (0.05–1.5 M). BPA in each fraction was assayed as described in Example 12. BPA was found in flow-through fractions (FIG. 14).

Example 18
Purification of SCGF through Red-Sepharose

The culture supernatants of KPB-M15 cells as described in Example 9 was dialyzed against 50 mM Tris-HCl buffer (pH 7.0) containing 50 mM NaCl. It was applied to a Red-Sepharose CL-6B (Pharmacia) column equilibrated with the same buffer, washed thoroughly with the same buffer, and eluted with a linear NaCl gradient (0–1.5 M). BPA in each fraction was assayed as described in Example 12. BPA was found in the later half of flow-through fractions (FIG. 15).

Example 19
Fractionation of SCGF through Sephacryl S-200HR

The active fractions eluted through the $Cu^{2+}$ chelating-Sepharose column shown in Example 14 were applied to a Sephacryl S-200HR (Pharmacia) column equilibrated with 20 mM phosphate buffer (pH 7.4) containing 0.15 M NaCl. BPA in each fraction was assayed as described in Example 7. BPA was found bimodally at broad range from 20 kD to 80 kD in molecular mass (FIG. 16).

Example 20
Sequential Purification of SCGF

The culture supernatants of KPB-M15 cells as described in Example 9 was diluted with 6.5 volumes of distilled water to adjust the isonic strength. It was applied to a DEAE-Sephacel column equilibrated with 20 mM HEPES-NaOH buffer (pH 6.0) containing 20 mM NaCl, washed thoroughly with the same buffer, and eluted with a linear NaCl gradient (0.02–0.5 M). Fractions eluted at 0.1–0.25 M NaCl were collected.

The DEAE-Sephacel fractions were applied to a $Cu^{2+}$ chelating Sepharose column equilibrated with 20 mM HEPES-NaOH buffer (pH 7.4) containing 0.5 M NaCl, washed thoroughly with the same buffer, and eluted with a linear glycine gradient (0–0.2 M). Fractions eluted at about 35 mM glycine were collected. The fractions were dialyzed against 20 mM HEPES-NaOH buffer (pH 6.0) containing 20 mM NaCl, applied to a DEAE-Sephacel mini-column equilibrated with the same buffer, washed thoroughly with the same buffer, and eluted with the same buffer containing 0.5 M NaCl.

The condensed fractions were applied to a Sephacryl S-200HR column for gel filtration. BPA in each fraction was bimodal as in Example 19.

The purified fractions through the gel filtration were applied to tandemly united columns of Blue-Sepharose CL-6B (upstream) and DEAE-Sephacel (downstream) both equilibrated with 20 mM HEPES-NaOH buffer (pH 7.0) containing 50 mM NaCl, washed thoroughly with the same buffer, then the upper column was detached, and eluted through the DEAE-Sephacel column with the same buffer containing 0.5 M NaCl. Table 1 shows BPA and protein recovery in the sequential purification.

TABLE 1

Summary of SCGF Purification

| | Volume (ml) | Absorbance at 280 nm | Total Absorbance at 280 nm | BPA (No. of Erythroid Bursts) |
|---|---|---|---|---|
| KPB-M15 Culture Supernatants | 1500 | — | — | 17 |
| Elution Fraction 1 through DEAE-Sephacel | 375 | 0.168 | 63 | — |

TABLE 1-continued

Summary of SCGF Purification

| | Volume (ml) | Absorbance at 280 nm | Total Absorbance at 280 nm | BPA (No. of Erythroid Bursts) |
|---|---|---|---|---|
| Elution Fraction through $Cu^{2+}$ chelating Sepharose | 29 | 0.221 | 6.4 | 35 |
| Elution Fraction 2 through DEAE-Sephacel | 1.84 | 1.9 | 3.5 | 25 |
| Elution Fraction through SephacrylS-200HR | 12.9 | 0.088 | 1.13 | 21 |
| Elution Fraction through Blue-DEAE | 3.9 | 0.075 | 0.29 | 30 |

Example 21
Amplification and Identification of a Human SCGF Variant by Reverse Transcriptase-Polymerase Chain Reaction DNA fragments were synthesized as primers according to the nucleotide sequences within the SCGF gene (SEQ ID NO: 2), are predicted to encode the N- and C-terminal portion of the mature protein. A reverse transcriptase-polymerase chain reaction (RT-PCR) was performed on mRNA from human bone marrow as a template using the primers. The oligonucleotides shown in SEQ ID NOs: 6 and 7 were used as the forward and reverse primer, respectively. The oligonucleotides were synthesized based on the solid phase synthesis using a fully automated DNA synthesizer. Each oligonucleotide was purified through an OPC cartridge. An sscDNA was synthesized with an oligo(dT) primer from poly $A^+$ RNA 1 µg from human bone marrow (Clontech) in reaction solution 20 µl according to the protocol of SuperScript™ Preamplification System Kit (GIBCO/BRL). PCR was performed with Taq DNA polymerase (2.5 units; Takara) in reaction solution 100 µl using a part of the sscDNA as a template. PCR was carried out in the presence of 10% DMSO using 50 µM forward and reverse primers. One PCR cycle consisted of denaturation at 94° C. for 1 minute, annealing at 55° C. for 2 minutes and extension at 72° C. for 2 minutes in that order; total 30 cycles in the present invention. The 30th extension was at 72° C. for 5 minutes. The RT-PCR products were fractionated by agarose gel electrophoresis. A DNA fragment around 960 bp was cut out from the gel, purified according to the protocol of QIA Quick Gel Extraction Kit (Qiagen), and eluted with TE buffer [10 mM Tris buffer (pH 8), 1 mM ethylenediamine tetraacetic acid disodium (EDTA) (pH 8)] 30 µl. The purified DNA fragment (9 µl) was inserted into pT7Blue(R) vector 1 µl according to the protocol of T-Vector Kit (Novagen). XL-1 Blue E. coli was transformed with the vector, and ampicillin-resistant cDNA-carrying E. coli was cloned. The RT-PCR product inserted in pT7Blue(R) vector was sequenced using DNA Sequencer Model 4000 (LI-COR). SequiTherm EXCEL™ Long-Read DNA Sequence Kit-LC (Epicentre Technologies) was used as specific reagents for sequencing according to the manufacturer's instructions. Five clones had identical nucleotide sequences. The nucleotide sequence predicted to encode the mature protein is shown in SEQ ID NO: 5 and its deduced amino acid sequence is shown in SEQ ID NO: 4. The cDNA was of an SCGF variant; 78 amino acids from position 196 to 273 in SEQ ID NO: 4 are added to position between 195 and 196 of SCGF (SEQ ID NO: 1).

Example 22
Cloning of Mouse SCGF cDNA
(1) Preparation of a cDNA Library from Mouse Stromal Cell Line MC3T3-G2/PA6 mRNA (about 30 µg) was prepared from mouse calvaria-derived stromal cell line MC3T3-G2/PA6 (1×10$^8$) (RIKEN Cell Bank: Accession No. RCB 1127) using Fast Track mRNA Extraction Kit (Invitrogen). The reagents were used according to the manufacturer's instructions. A double-stranded (ds) cDNA was synthesized with oligo(dT) primers from the mRNA (5 µg) using cDNA Synthesis System (GIBCO/BRL). cDNA fragments of about 1.5 kb –2.2 kb were recovered by agarose gel electrophoresis. Super-Script™ RNase H⁻ RTase (Invitrogen) was used instead of Moloney Murine Leukemia Virus (M-MLV) RTase in the Extraction Kit. The ssDNAs for the SfiI linker 11 mer (SEQ ID NO: 10) and 8 mer (SEQ ID NO: 11) were synthesized using 380A/DNA synthesizer (Applied Biosystems), and 50 µg each was phosphorylated with T4 polynucleotide kinase (Takara). The phosphorylated linkers (11 mer: 4 µg and 8 mer: 2.9 µg) were ligated to the dscDNA synthesized above, and subjected to agarose gel electrophoresis to recover dscDNA fragments of about 1.5 kb–2.2 kb. A cloning vector, pAMoPRC3Sc (Japanese Unexamined Patent Publication No. 06-823021; Sasaki et al., J. Biol. Chem. 268, 22782–22787, 1993) 24 µg was digested with SfiI and subjected to agarose gel electrophoresis to recover DNA fragments of about 8.8 kb. The pAMoPRC3Sc-derived SfiI fragment (8.8 kb) 2 µg was ligated to the dscDNA purified above, mixed with transfer RNA (tRNA) 5 µg, and ethanol-precipitates were dissolved in TE buffer 20 µl. LE392 E. coli (Maniatis et al., Molecular Cloning: A Laboratory Manual, Cold Springs Harbor Press, Plain View, N.Y., 2nd Ed., 1989) was transformed with the above DNA solution by electroporation (William et al., Nucleic Acids Res., 16, 6127–6145, 1988) to obtain about 250,000 clones of an ampicillin-resistant AMo(PA6) cDNA library.

(2) Cloning of Mouse SCGF cDNA

The ampicillin-resistant AMo(PA6) cDNA library clones were individually distributed, 20,000 to a pool, to make up a total of 50 pools. Plasmid was prepared from each pool by alkaline lysis procedure. PCR was carried out with the plasmid DNA as a template and Taq polymerase (Takara), using a forward primer (SEQ ID NO: 6) and a reverse primer (SEQ ID NO: 7). One PCR cycle consisted of denaturation at 94° C. for 1 minute, annealing at 55° C. for 2 minutes and extension at 72° C. for 2 minutes in that order; total 30 cycles in the present invention. The 30th extension was at 72° C. for 5 minutes. The RT-PCR products were fractionated by agarose gel electrophoresis.

Ampicillin-resistant clones in pool No. 21 exhibited DNA amplification at about 960 bp, and re-seeded onto 96-well plates at a density of about 300 clones/well. PCR was performed with the E. coli DNA in each sub-pool as a template. Pool No. 1C4 exhibited DNA amplification at about 960 bp, then the ampicillin-resistant clones in the pool were re-seeded so as to contain 1 clone/well. Clone No. 21-1C4-5H6 exhibited DNA amplification. The nucleotide sequence of the clone was determined using DNA Sequencer Model 4000 (LI-COR) as in Example 21. The nucleotide sequence predicted to encode the mature protein in SEQ ID NO: 9 and its deduced amino acid sequence in SEQ ID NO: 8. The cDNA was of a mouse SCGF which is highly homologous with the human SCGF variant cDNA.

Example 23
Cloning of Rat SCGF

DNA fragments predicted to encode untranslated regions within the mouse SCGF gene (SEQ ID NO: 9) were synthesized as primers. RT-PCR was performed on a sscDNA prepared from the RNA of rat osteosarcoma cell line ROS-17/2.8-5 (RIKEN Cell Bank: Accession No. RCB0462) as a template using the above primers. ROS-17/2.8-5 cells were cultured in 60 mm plates until confluent. Total RNA was prepared from the cells using ISOGEN solution (Nippon Gene, Toyama Pref.) 1 ml. An sscDNA was synthesized with an oligo(dT) primer from the total RNA 5 µg in reaction solution 20 µl according to the protocol of SuperScript™ Preamplification System Kit (GIBCO/BRL). PCR was performed with EX Taq DNA polymerase (2.5 units; Takara) in reaction solution 100 µl using a part of the sscDNA as a template and 50 µM forward and reverse primers. The oligonucleotides shown in SEQ ID NOs: 14 and 15 were used as a forward and reverse primer, respectively, which were prepared using a fully automated DNA synthesizer, and purified through an OPC cartridge. One PCR cycle consisted of denaturation at 94° C. for 1 minute, annealing at 55° C. for 2 minutes and extension at 72° C. for 2 minutes in that order; total 30 cycles in the present invention. The 30th extension was at 72° C. for 5 minutes. The RT-PCR products were fractionated by agarose gel electrophoresis. A DNA fragment around 960 bp was cut out from the gel, purified according to the protocol of QIA Quick Gel Extraction Kit (Qiagen), and eluted with TE buffer 30 µl. The purified DNA fragment (9 µl) was inserted into pT7Blue(R) vector 1 µl according to the protocol of T-Vector Kit (Novagen). XL-1 Blue E. coli was transformed with the vector, and ampicillin-resistant cDNA-carrying E. coli was cloned. The RT-PCR product inserted in pT7Blue(R) vector was sequenced using DNA Sequencer Model 4000 (LI-COR). SequiTherm EXCEL ™ Long-Read DNA Sequence Kit-LC (Epicentre Technologies) was used as specific reagents for sequencing according to the manufacturer's instructions. Five clones had identical nucleotide sequences. The nucleotide sequence predicted to encode the mature protein is shown in SEQ ID NO: 13 and its deduced amino acid sequence in SEQ ID NO: 12. The cDNA was of a rat SCGF highly homologous with the human SCGF variant cDNA.

Example 24
Structural Analysis of Human SCGF Polypeptide Produced in Animal Cells
(1) Construction of Plasmid pAGE-SCGFβ for the Expression of Human SCGF in an Animal Cell Human expression vector pAGE-SCGF β was constructed by ligation of a HindIII-KpnI fragment from the known mammalian expression vector pAGE210 (WO96-34016) to the DNA SEQ ID NO: 2 encoding the SCGF polypeptide (FIG. 17).

Briefly, pAGE210 3 µg was digested with HindIII and KpnI, and fractionated by agarose gel electrophoresis. A DNA fragment around 9 kb was cut out from the gel, purified according to the protocol of QIA Quick Gel Extraction Kit (Qiagen), and eluted with TE buffer 30 µl.

A cDNA encoding the mature protein (SEQ ID NO: 1) was prepared by PCR from the human SCGF cDNA (clone No. 116-10C) described in Example 7. PCR was carried out on human SCGF cDNA clone No. 116-10C (about 100 ng) as a template in reaction solution 50 µl with Native Pfu polymerase (1.25 units; Stratagene) and 10% DMSO, using 50 µM forward and reverse primers. The oligonucleotides shown in SEQ ID NOs: 14 and 15 were used as a forward and reverse primer, respectively, which were synthesized using a fully automated DNA synthesizer, and purified through an OPC cartridge. One PCR cycle consisted of denaturation at 94° C. for 1 minute, annealing at 50° C. for 1 minutes and extension at 72° C. for 2 minutes; total 30 cycles in the present invention. The 30th extension was at 72° C. for 5 minutes. The RT-PCR products were phenol chloroform-extracted, ethanol-precipitated, digested with HindIII and KpnI, and fractionated by agarose gel electrophoresis. A DNA fragment around 770 bp was cut out from the gel, purified and eluted with TE buffer. The HindIII-KpnI fragment of the PCR product was ligated to the HindIII-KpnI fragment of pAGE210 above. DH5 α E. coli (Clontech) was transformed with the DNA to develop plasmid pAGE-SCGF β shown in FIG. 17, where abbreviations include; pSE, SV40 early promoter, Hyg; hygromycin resistance gene, dhfr; dihydrofolate reductase gene, P1, pBR322-derived P1 promoter, Ptk, Herpes simplex virus (HSV) thymidine kinase (tk) promoter, SP.BG; rabbit β globin gene splicing signal, ABG, rabbit β globin gene poly(A) addition signal, and ASE; SV40 early gene poly(A) addition signal.

(2) Expression of Human SCGF Polypeptide Gene in Animal Cells

The introduction of a plasmid into animal cells was performed by electroporation according to the method of Miyaji et al. (Miyaji et al., Cytotechnology, 3, 133–140, 1990). pAGE-SCGB 4 μg obtained in (1) above was introduced into $4 \times 10^6$ dhfr gene-deleted CHO cells (Urlaub and Chasin, Proc. Natl. Acad. Sci. USA, 77, 4216–4220, 1980). The cells were suspended in MEMα 2000-dFCS(5) 10 ml [MEMα 2000 medium (GIBCO/BRL) containing 5% dFCS, 1/40 volume of 7.5% $NaHCO_3$, 3% L-glutamine solution (200 mM; GIBCO/BRL), 0.5% penicillin/streptomycin solution (GIBCO/BRL; 500 units/ml penicillin and 5000 μg/ml streptomycin)], and incubated in 10-cm plates (Iwaki Glass) at 37° C. under 5% $CO_2$ in air for 24 hours. Hygromycin (GIBCO/BRL) was added at a concentration of 0.3 mg/ml, and the cells were cultured for 1 to 2 weeks. Transformed cells were harvested at the time of confluence, suspended in MEMα 2000-dFCS(5) containing 0.3 mg/ml hygromycin and 50 nM methotrexate (MTX) at a density of $1-2 \times 10^5$/ml, and distributed into F75 flasks (Greiner) by 2-ml aliquots. After 1 to 2-week culture, 50 nM MTX-resistant clones were suspended in MEMα 2000-dFCS(5) containing 0.3 mg/ml hygromycin and 200 nM MTX at a density of $1-2 \times 10^5$/ml, distributed into F75 flasks by 2-ml aliquots. After another 1 to 2 week culture, 200 nM MTX-resistant clones were suspended in MEM α 2000-dFCS(5) containing 200 nM MTX at a density of $1-2 \times 10^5$/ml, distributed into F75 flasks by 15 ml aliquots, and further cultured for 5–7 days. When the resistant clones became 80–100% confluent, the medium was exchanged with a serum-free medium for CHO cells 15 ml (EX-cell 301 medium from JRH Biosciences). After 4-day culture, culture supernatants containing SCGF polypeptide were harvested by contrifugation.

(3) Preparation of Anti-SCGF Polyclonal Antibody (SEQ ID NO: 17)

An origo peptide Ac-Arg-Glu-Trp-Glu-Gly-Gly-Trp-Gly-Gly-Ala-Gln -Glu-Glu-Glu-Arg-Glu-Arg-Glu-Ala-Leu-Cys ("Ac-Arg" indicates acetylarginine) corresponding to the amino acids at position 27–46 From the SCGF polypeptide (SEQ ID NO: 1) was solidphase-synthesized by the Fmoc method (Fields and Noble, Int. J.PeptideProteinRes., 35: 161–214, 1990) using a Shimadzu automatic peptidesynthesizer Model PSSM-8 according to the manufacturer's synthesis program.

The synthetic peptide was crosslinked to Keyhole Lympet hemocyanin(KLH;Calbiochem) using m-maleimide-benzoyl-n-hydroxysuccyl (MBS; Nacalai Tesque) to improve its immunogenicity. Cys at the C-terminal of the syntheric peptide was favorable in reaction with MBS.

One tenth volume of MBS was added dropwise to 10 mg/ml KLH in PBS, and agitated at room temperature for 30 minutes. Free MBS was removed through a Sephadex G-25 column pre-equilibrated with PBS. KLH-MBS 2.5 mg was mixed with the synthetic peptide 1 mg in 0.1 M phosphate buffer, agitated at room temperature for 3 hours, and dialyzed against PBS containing 0.5 M NaCl. Five-week old female SD rats were immunized with the KLH-peptide 100 μg plus aluminium gel 2 mg and $1 \times 10^9$ pertussis vaccine (ChibaPre.Serum Institute). Two weeks thereafter, the KLH-peptide 100 μg alone was administered once aweek 4 times in total. Three days after the final boost, whole blood was obtained to prepare a polyclonal antibody.

(4) Western Blotting

The CHO culture supernatants obtained in (2) above was fractionated by sodium clodecylsulfate polyacrylamide gel electrophoresis (SDS-PAGE), and transferred Immobilon Transfer Membrane (Millipore) by the semi-dry blotting method. It was soaked in advance 100% methanol for 20 seconds,then in a solution containing 10 mM CAPS, 10% methanol and 0.03% SDS (pH 11.0) for over 30 minutes. After blotting at 2 $mA/cm^2$ for 2 hours, the membrane was shaken in a blocking solution 200 ml[PBS buffer (137 mM NaCl, 2.7 mM KCl, 9.6 mM $Na_2$ $HPO_4$ $KH_2PO_4$)(pH 7.2)containing 1% BSA]for 1 hour and washed once with PBS. The membrane was placed in a vinyl bag together with 1:500-diluted anti-SCGF polyclonal antibody (antiserum) prepared in (3) above. The bag was sealed and shaken at room temperature for 2–3 hours. Subsequently, the membrane was washed twice with 0.05% Tween 20-containing PBS for 5 minutes and once with PBS for 5 minutes. It was soaked in PBS 4 ml containing 0.65 g/ml peroxidase-labelled anti-rat IgG antibody(anti-rat immunoglobulin 1.3 g /liter; DAKO-immunoglobulins a/s) (i.e. 1:2000-diluted secondary antibody) and placed in avinyl bag. The bag was sealed and shaken at room temperature for 1 hour. The membrane was washed twice with 0.05% Tween 20-containing PBS for 5 minutes and once with PBS for 5 minutes.

Antibody-bound proteins were chemiluminescently analyzed using ECL Western Blotting Detection Reagents (Amersham). A specific band was detected at around 43 kDa.

(5) Purification of SCGF from the CHO Cell Culture Supernatants

First Step: Ammonium Sulfate Precipitation

Ammonium sulfate 17.25 g was added to the CHO cell culture supernatants 98 ml obtained in (2) above (30% ammonium sulfare at final concentration), agitated, and left at 4° C. for 2 hours. The solution was centrifuged at 18800 G for 30 minutes. Ammonium sulfate 13.44 g was added to the supernatant(50% ammonium sulfate at final concentration), agitated, and left at 4° C. for 2 hours. The solution was centrifuged at 18800 G for 30 minutes.

The precipitates were dissolved in 0.5 M NaCl-containing 20 mM sodium phosphate buffer (pH 7.2) 9 ml and purified by $Zn^{2+}$ chelating-Sepharose chromatography.

Second Step: $Zn^{2+}$ Chelating-Sepharose Chromatography

The precipitates obtained in the first step was applied to a $Zn^{2+}$ chelating-Sepharose Fast Flow column (5 mm×50 mm; Pharmacia) equilibrated with 0.5 M NaCl-containing 20 mM sodium phosphate buffer (pH 7.2), washed thoroughly with the same buffer, and eluted with a linear histidine gradient (0–0.25 M). The eluted fractions were assayed for antibody binding activity as shown in (4) above. The fractions eluted with 0.06 M–0.15 M histidine exhibited a specific antibody.

Third Step: MonoQ Anion Exchange Chromatography

The active fractions obtained in the second step were concentrated with Centricon-10 ultrafiltration membrane (Millipore). It was diluted with 10 volumes of 10 mM Tris-HCl (pH 7.0), applied to a MonoQ PC1.6/5 column (1.6 mm×50 mm; Pharmacia) equilibrated with 10 mM Tris-HCl (pH 7.0), washed thoroughly with the same buffer, and eluted with a linear NaCl gradient (0–1 M). The eluted fractions were assayed for antibody binding activity as shown in (4) above. The fractions eluted at about 0.5 M NaCl exhibited a specific activity. The active fraction was subjected to SDS-PAGE under reducing condition with 2-ME and silver stained (2D-Silver Staining Reagent-II "Daiichi"; Daiichi Pure Chemical). A band was detected at around 43 kDa as shown at lane 2 in FIG. 18; Lane 1 is a molecular weight marker; numerls represent molecular sizes. An arrow indicates the purified human SCGF.

(6) Structural Analysis of the SCGF Purified from the CHO Cell Culture Supernatants The N-terminal amino acid sequence of the purified SCGF was analyzed by conventional methods. Briefly, the purified fraction obtained in (5) above was subjected to SDS-PAGE under reducing condition with 2-ME and electrically transferred to a PVDF membrane (ProBlott; Perkin Elmer) according to the method of P. Matsudaira (J. B. C., 262, 10035–10038, 1987). The membrane was stained with Coomassie Brilliant Blue, and a band around 43 kDa positive in the Western blotting shown in (4) above was cut out. The N-terminal amino acid sequence of the band was analyzed with a gas phase protein sequencer (Procise Mode 1494; Perkin Elmer) according to the manufacturer's instructions. The amino acid sequence (SEQ ID NO: 16) was compatible with the amino acids from position 22 (from the N-terminus) of the amino acid sequence (SEQ ID NO: 1) deduced from the SCGF nucleotide sequence.

Effect of the Invention

The present invention provides a novel polypeptide possessing growth activities on hematopoietic stem cells, a gene encoding the polypeptide and an antibody reacting specifically with the polypeptide, as well as a method for isolating the above gene and a vector for use in the method.

Figure 1:
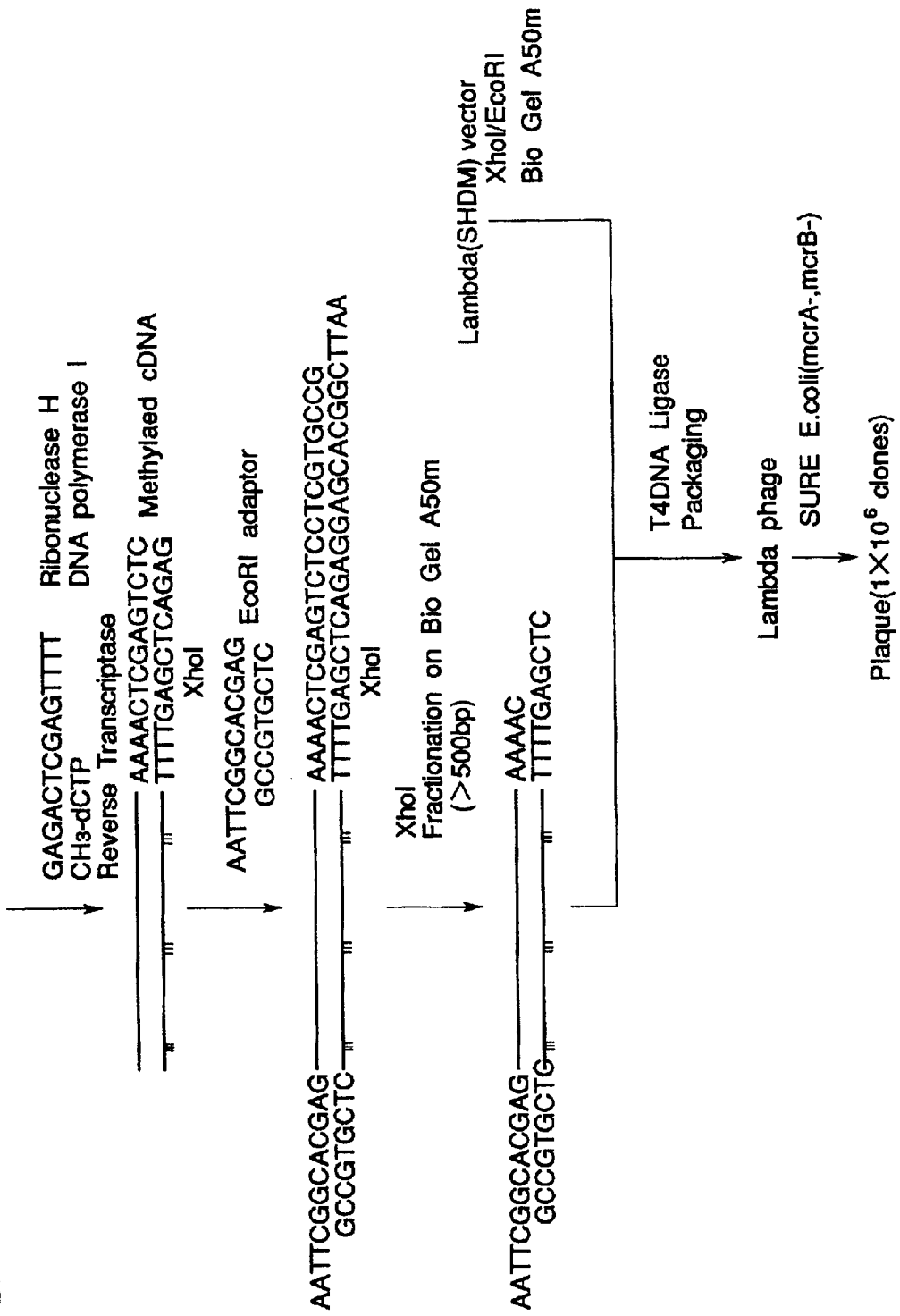
FIG. 1: a diagram showing an outline of cDNA synthesis SEQ ID NOS 18–22, respectively.
Figure 2:
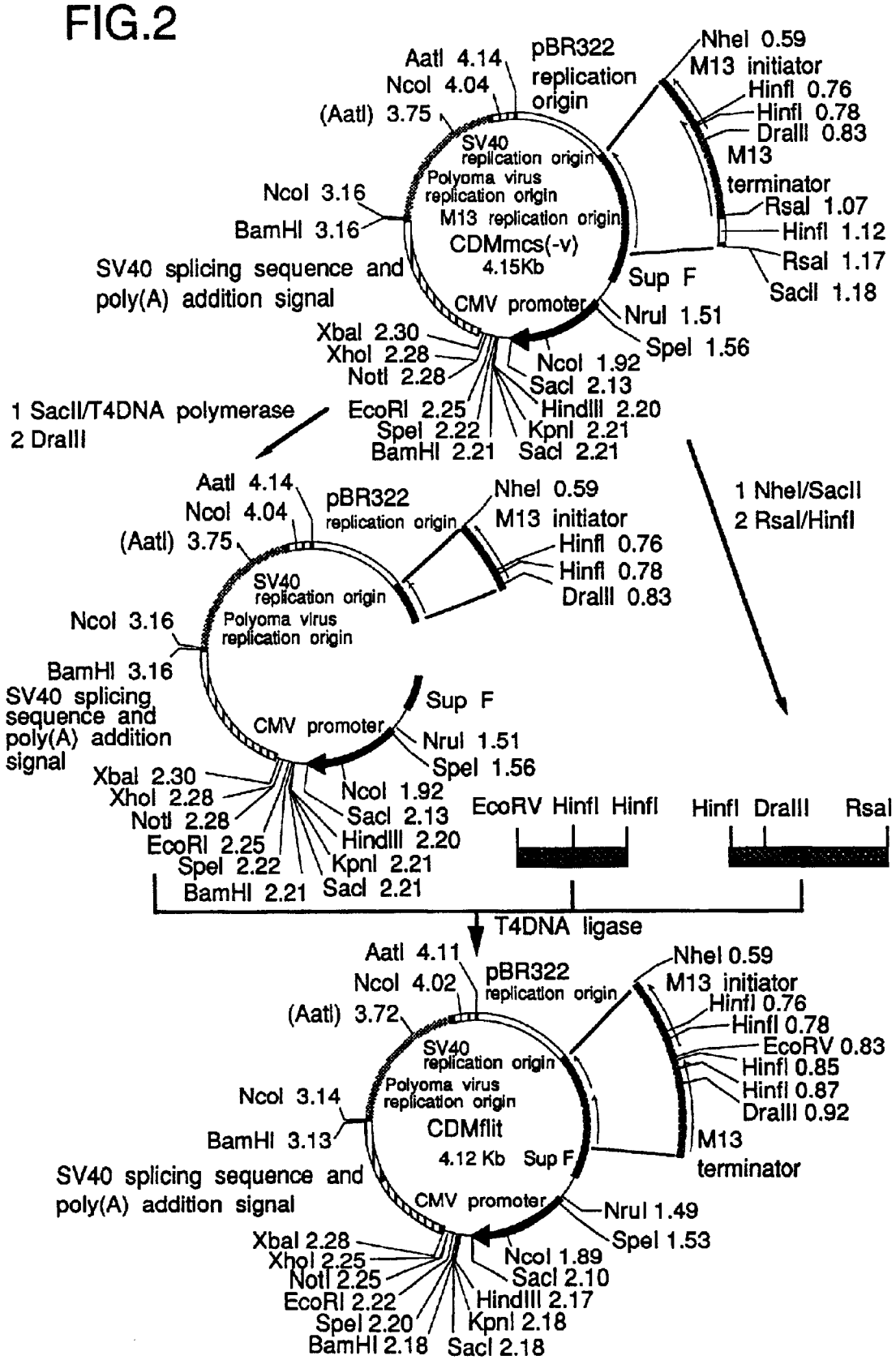
FIG. 2: a diagram illustrating the process for constructing CDMflit.
Figure 3:
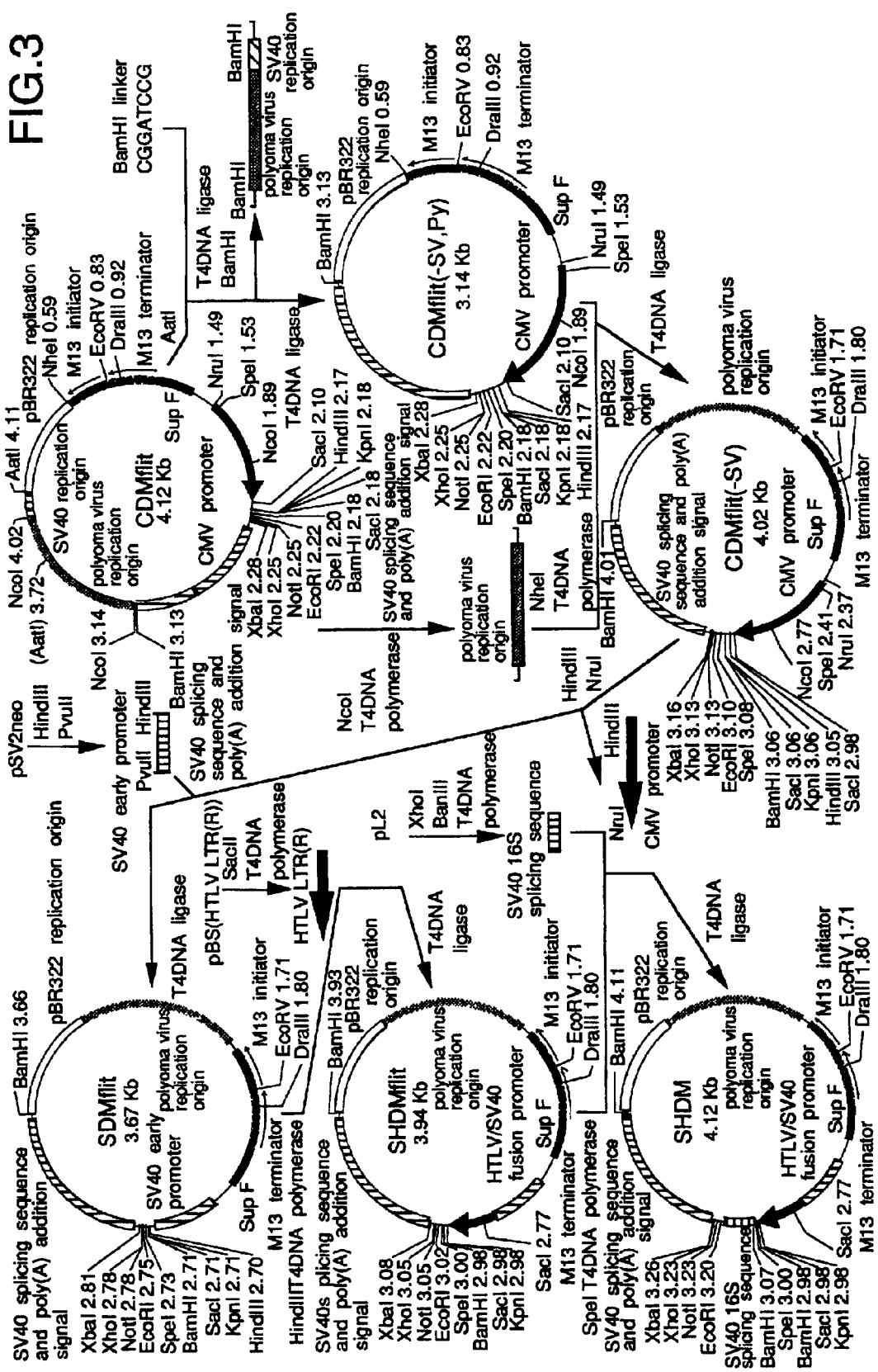
FIG. 3: a diagram illustrating the process for constructing SHDM.
Figure 4:
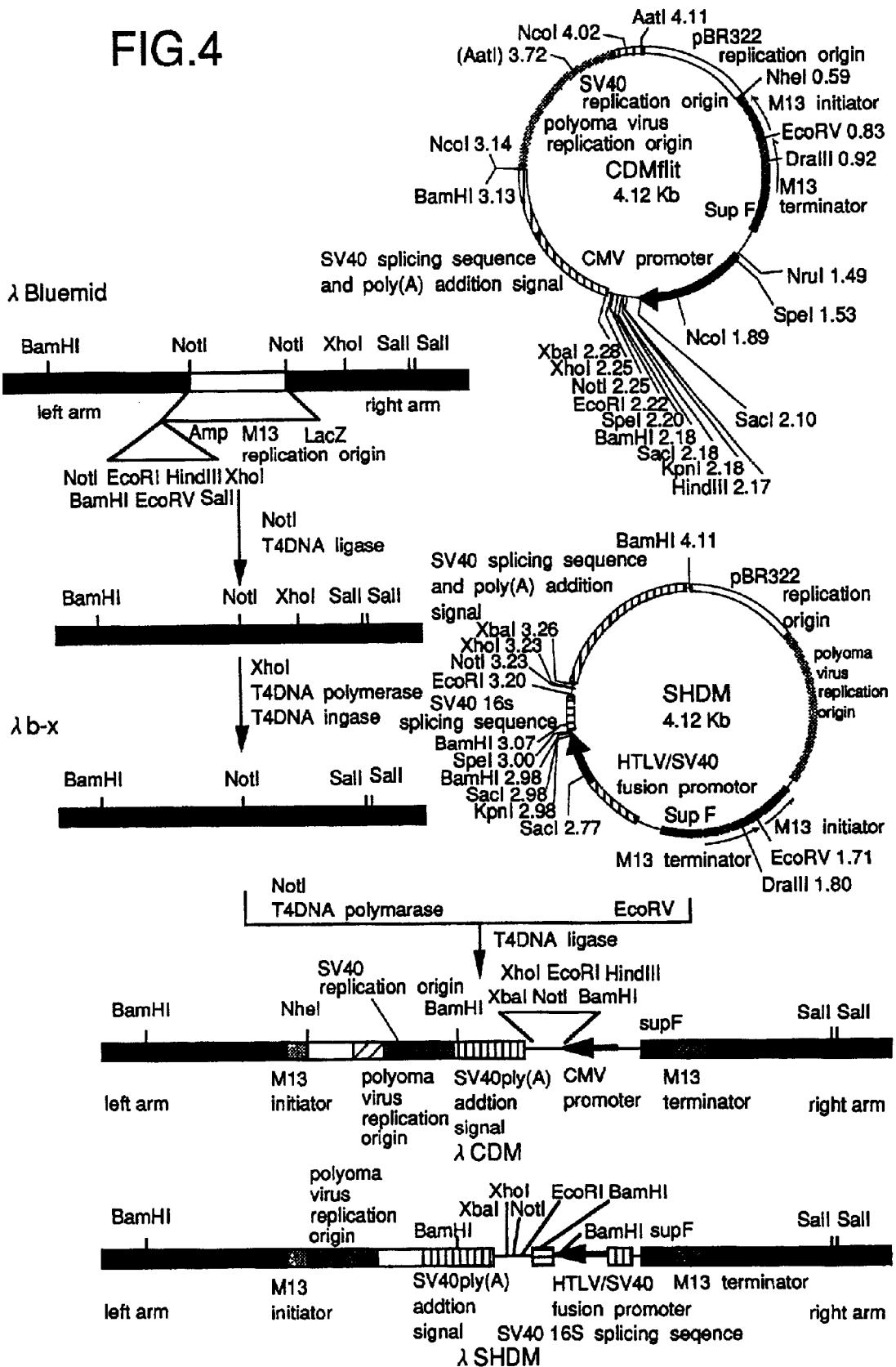
FIG. 4: a diagram illustrating the processes for constructing λ CDM and λ SHDM.
Figure 5:
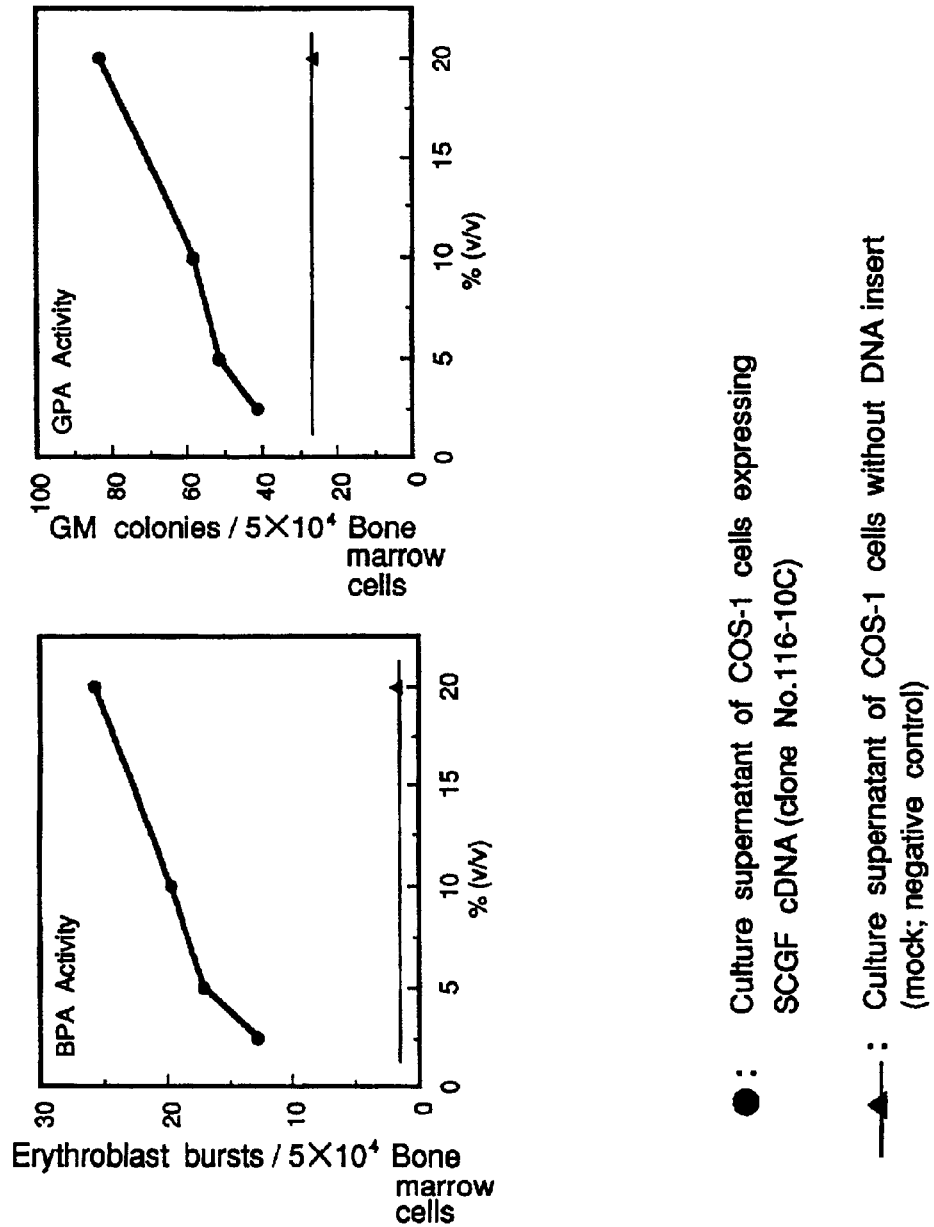
FIG. 5: graphs showing the activities of the polypeptide of the invention expressed in COS-1 cells.
Figure 6:
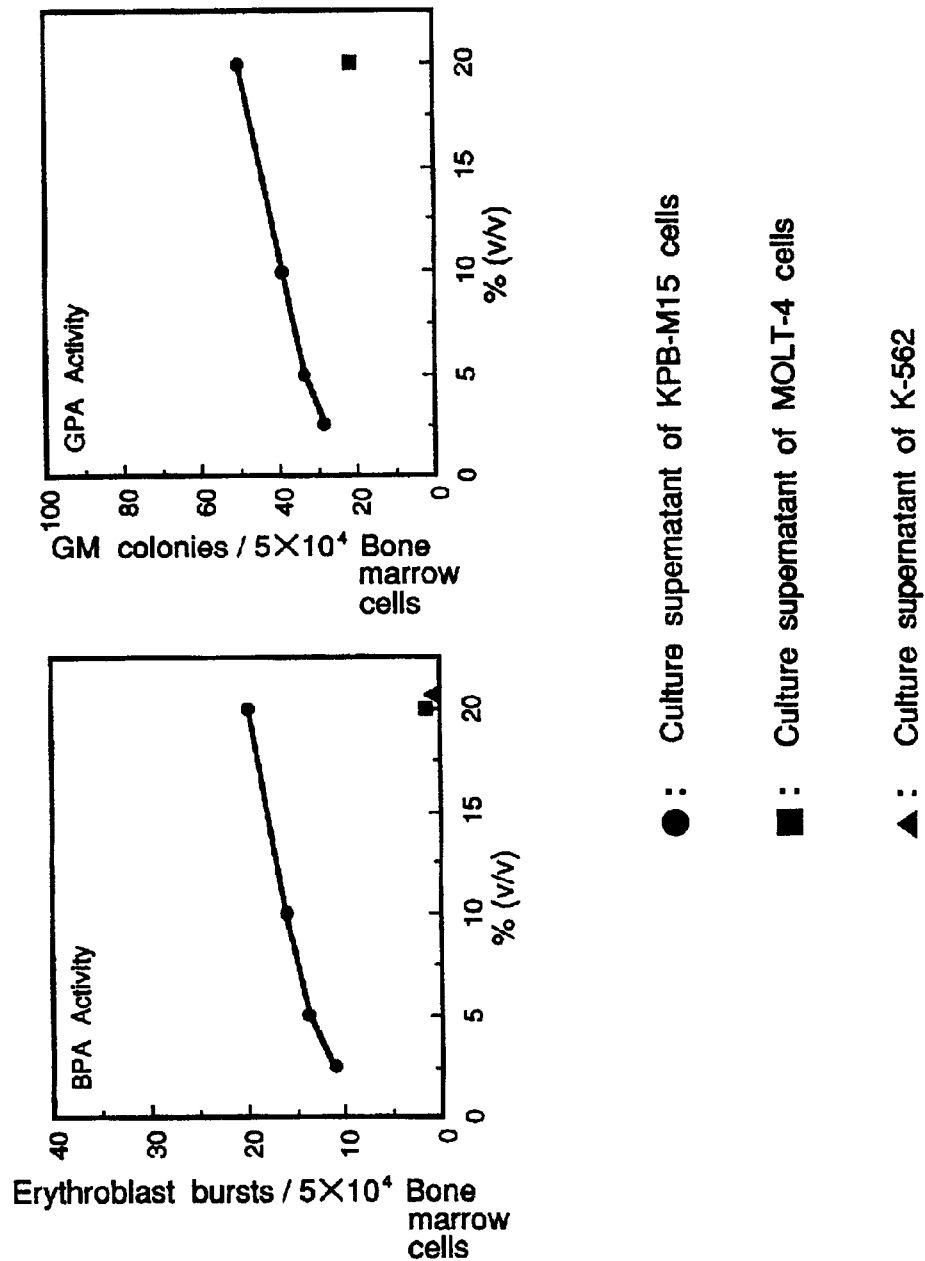
FIG. 6: graphs showing the activities of the polypeptide of the invention produced by KPB-M15 cells.
Figure 7:
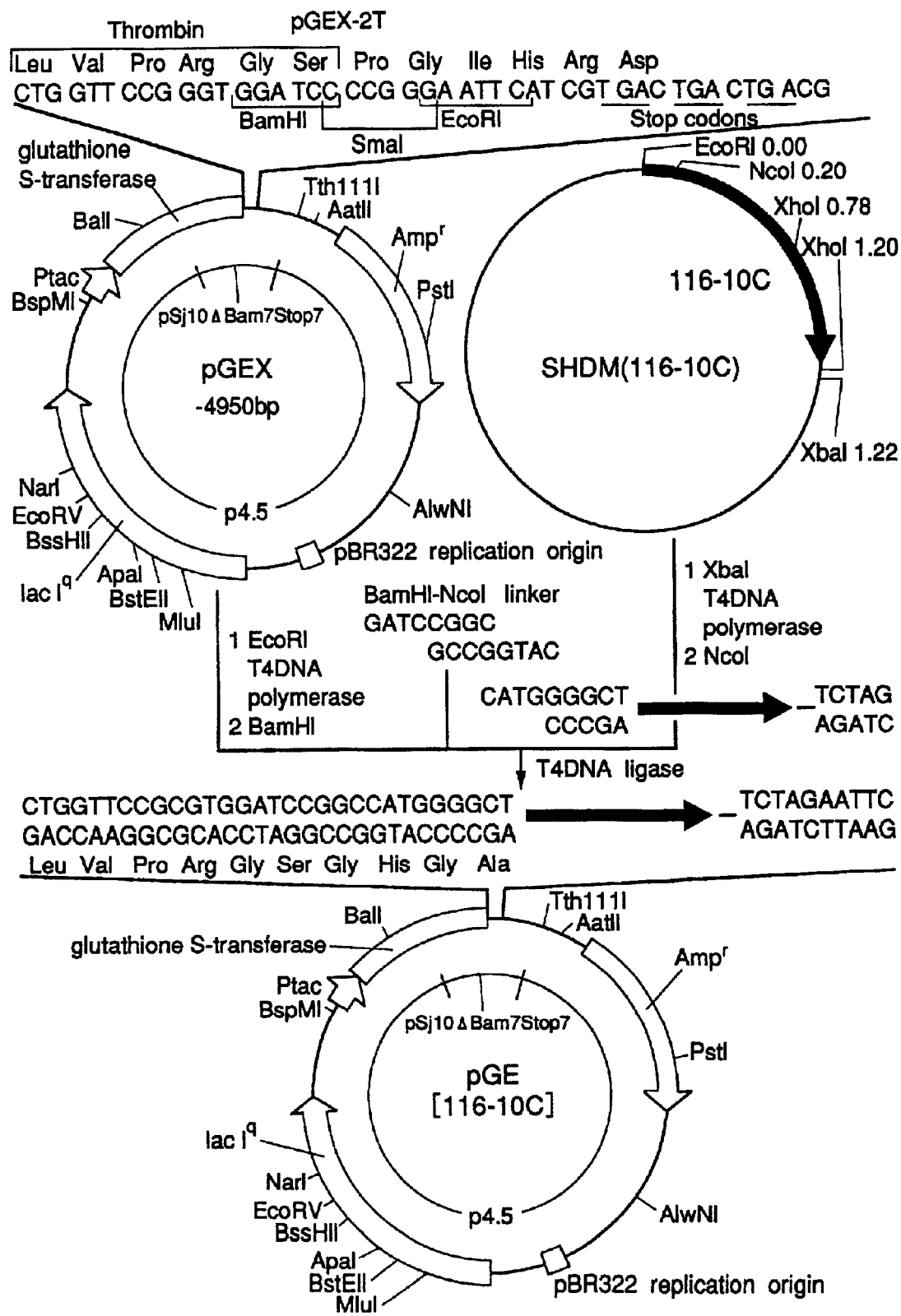
FIG. 7: a diagram illustrating the construction of expression vector for GST/116-10C fusion protein SEQ ID NOS 23–24 and 25–26, respectively.
Figure 8:
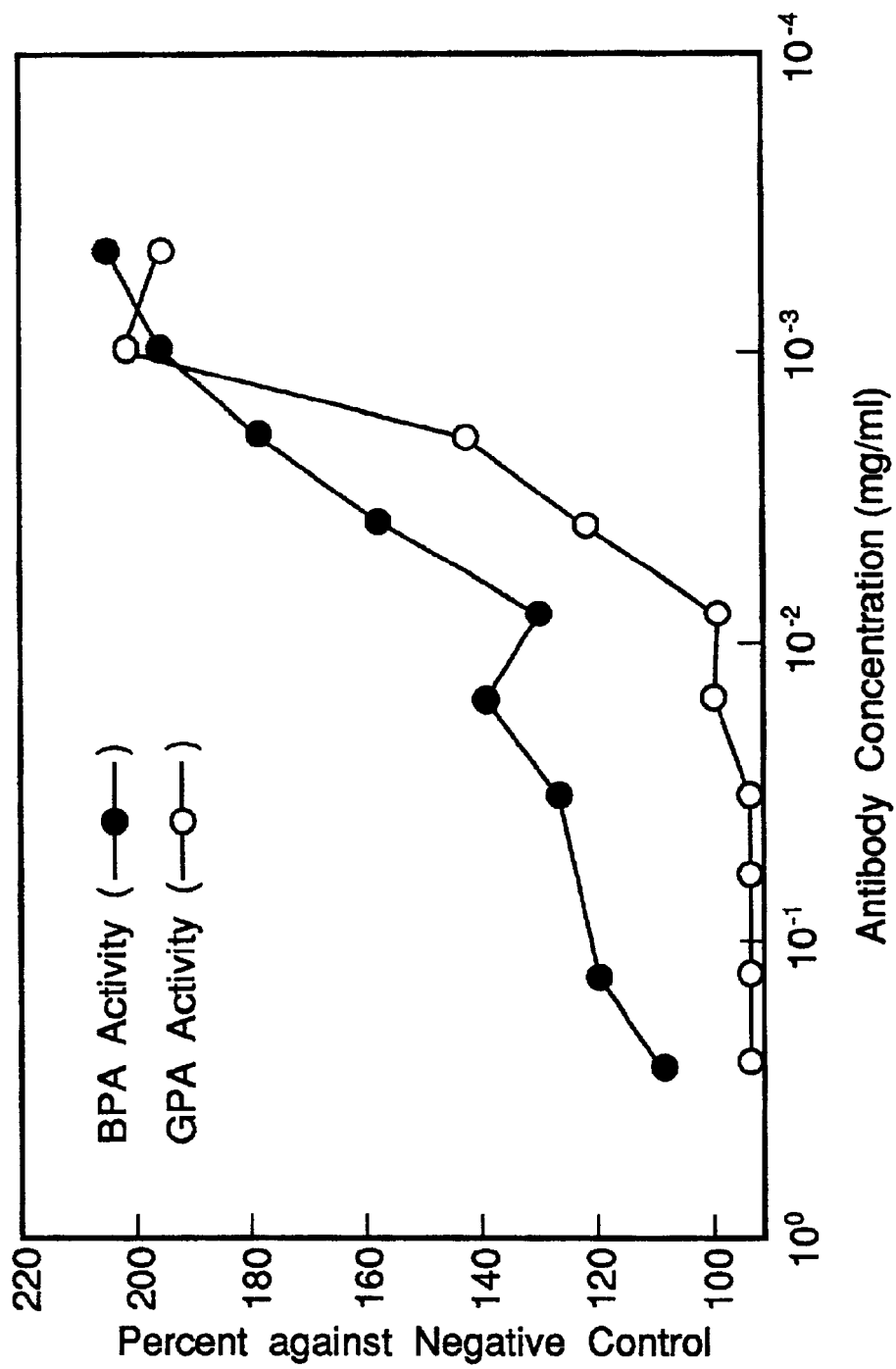
FIG. 8: a graph showing the neutralizing effect of anti-SCGF monoclonal antibody on the activities of the polypeptide of the invention.
Figure 9:
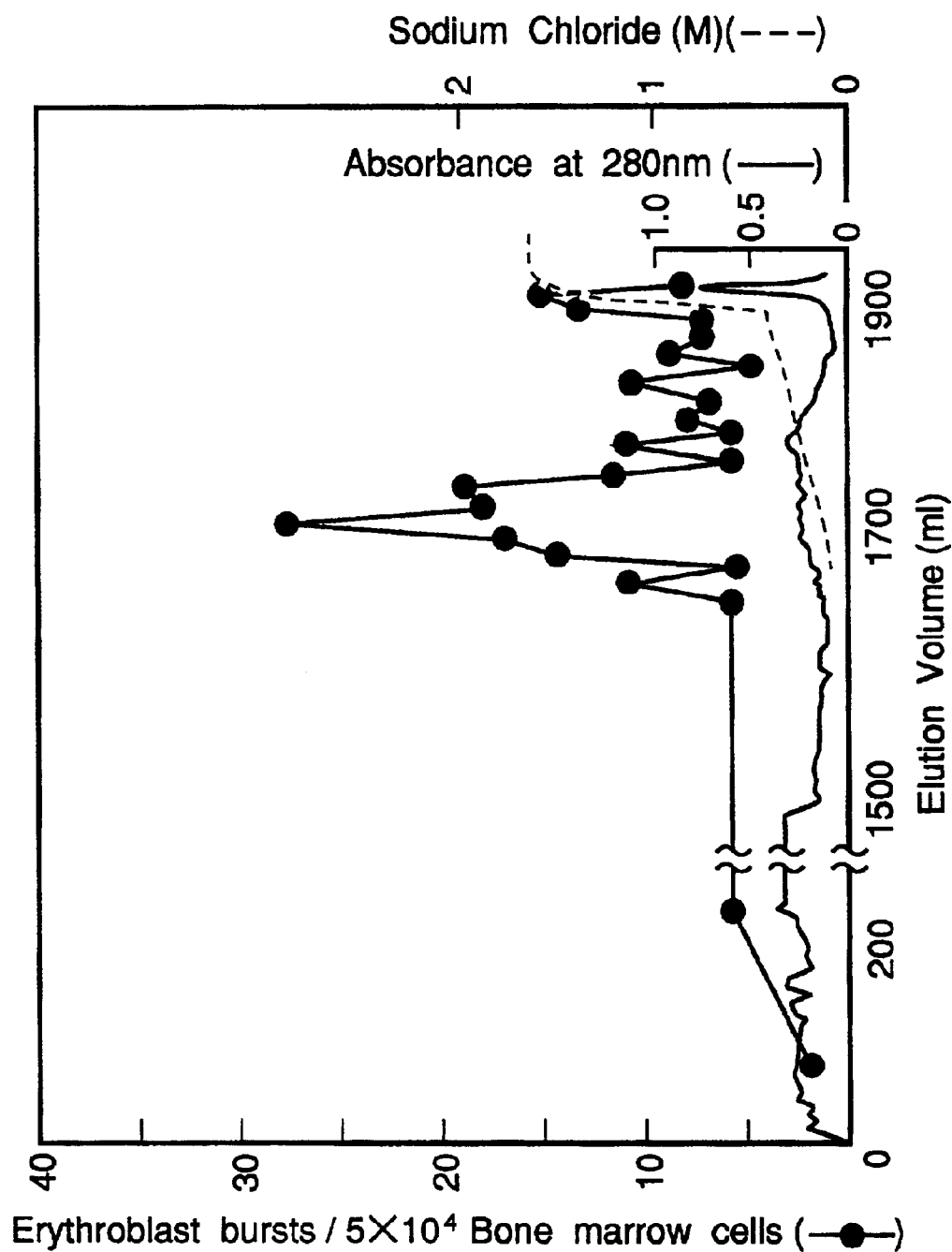
FIG. 9: a graph showing fractionation of the polypeptide of the invention through DEAE-Sephacel.
Figure 10:
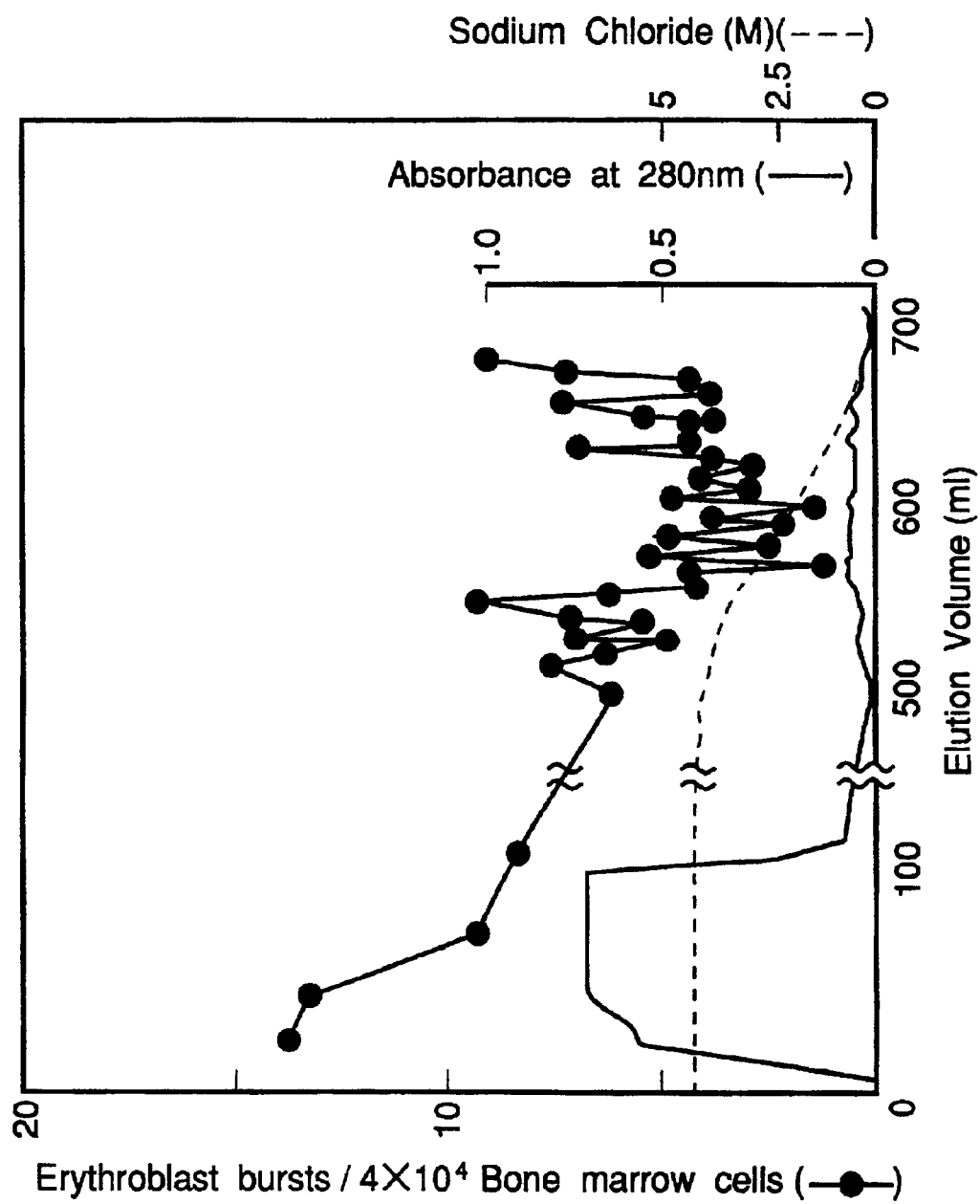
FIG. 10: a graph showing fractionation of the polypeptide of the invention through Octyl-Sepharose.
Figure 11:
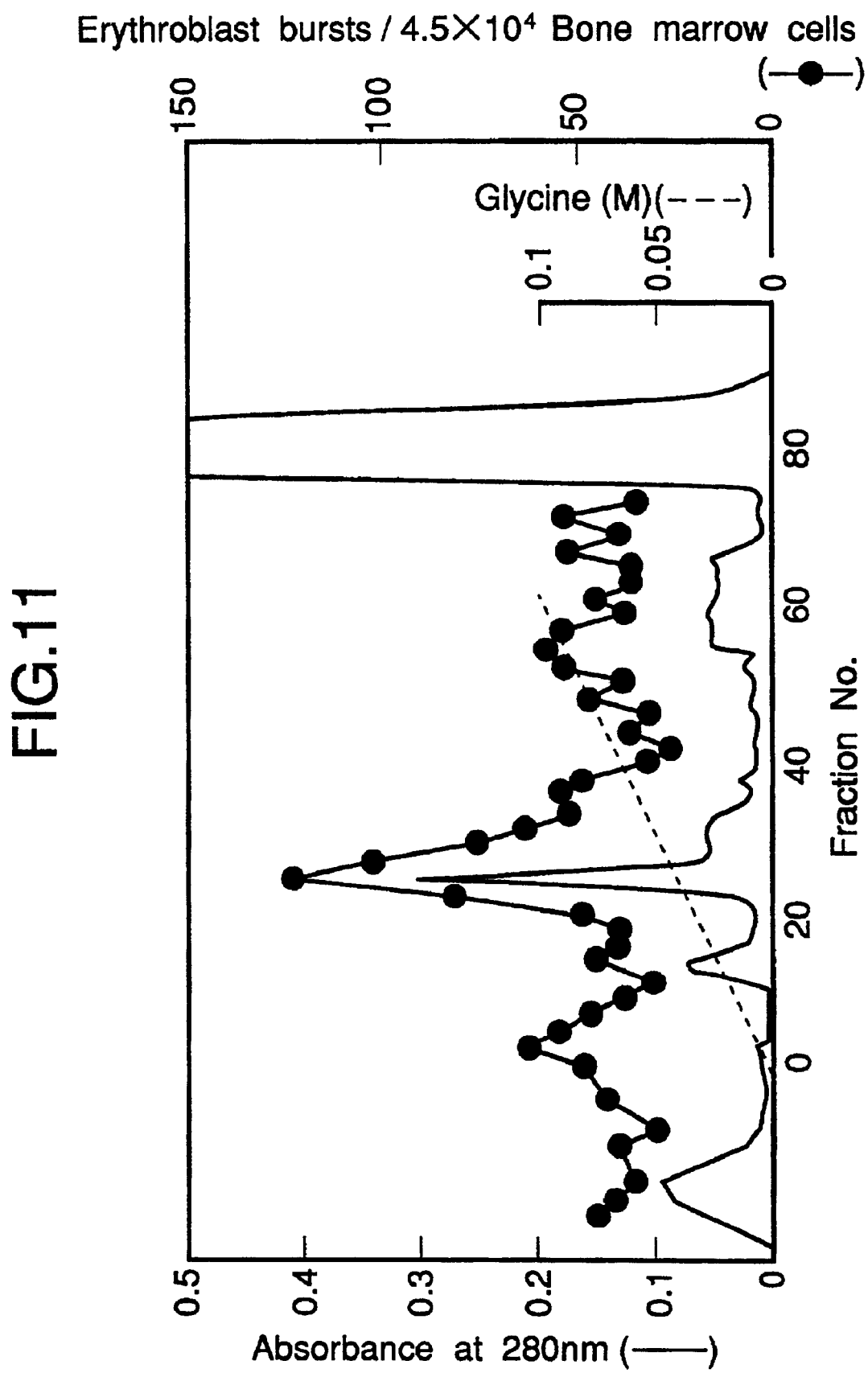
FIG. 11: a graph showing fractionation of the polypeptide of the invention through $Cu^{2+}$ chelating-Sepharose.
Figure 12:
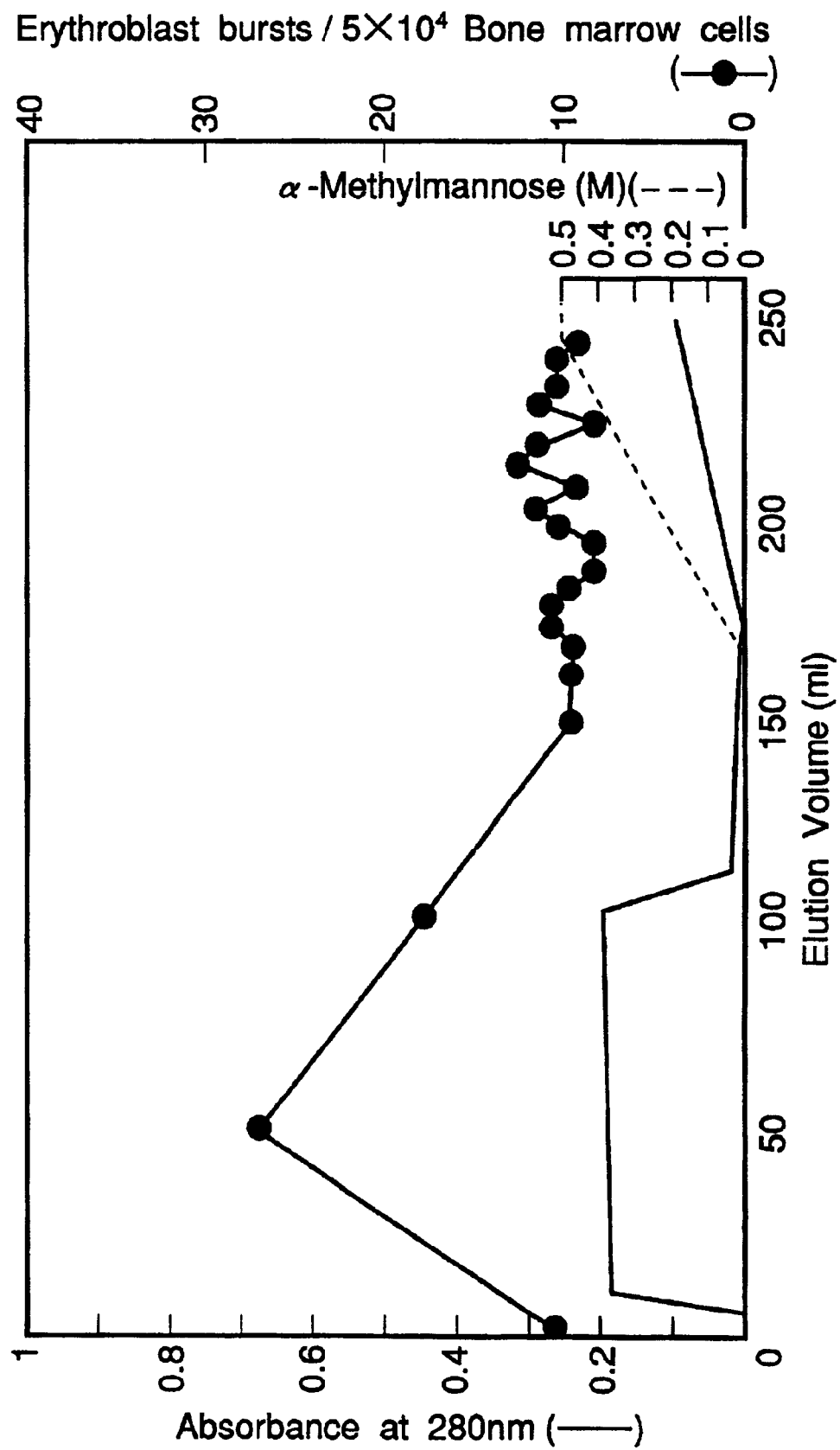
FIG. 12: a graph showing fractionation of the polypeptide of the invention through ConA-Sepharose.
Figure 13:
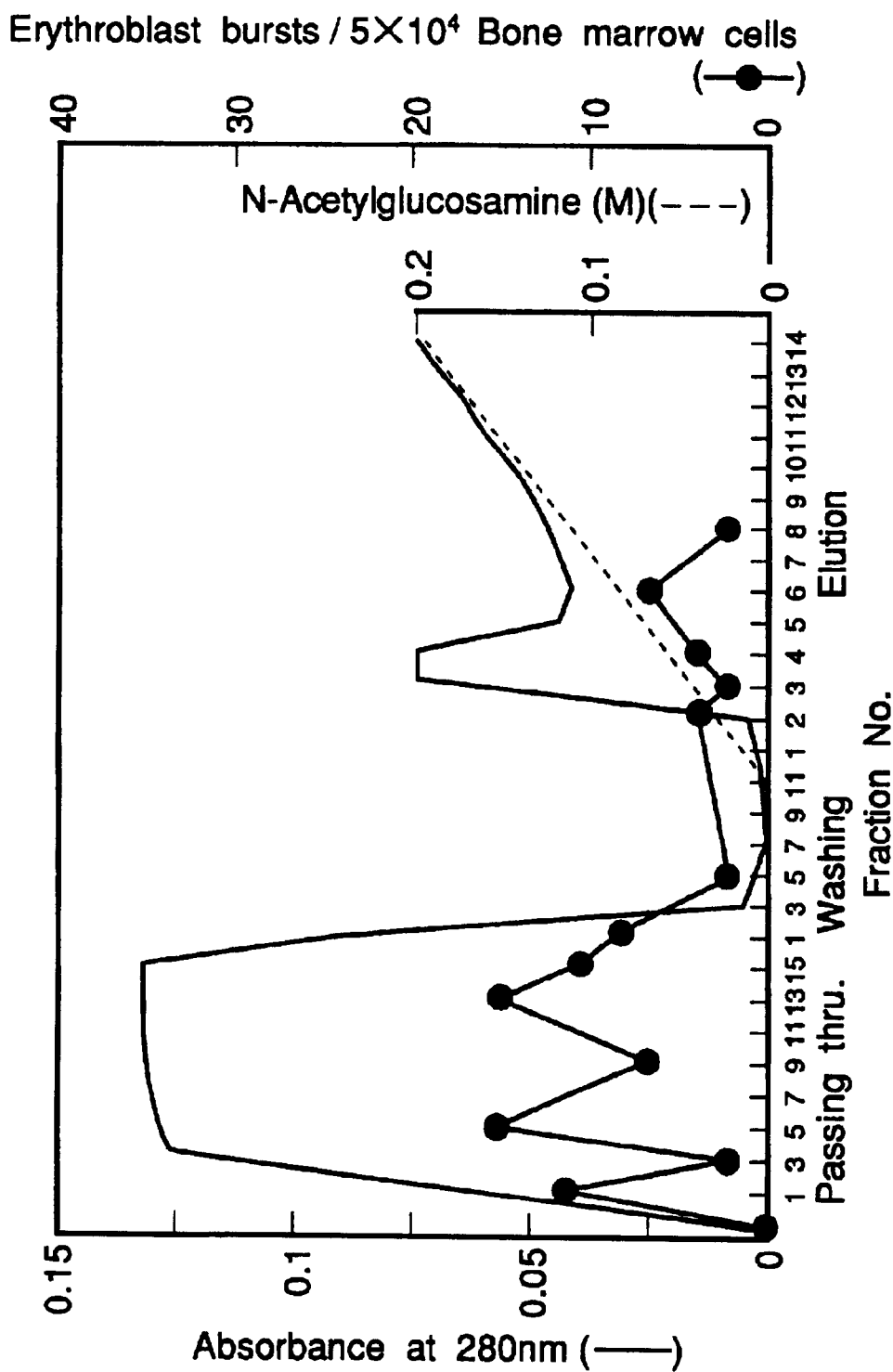
FIG. 13: a graph showing fractionation of the polypeptide of the invention through WGA-agarose.
Figure 14:
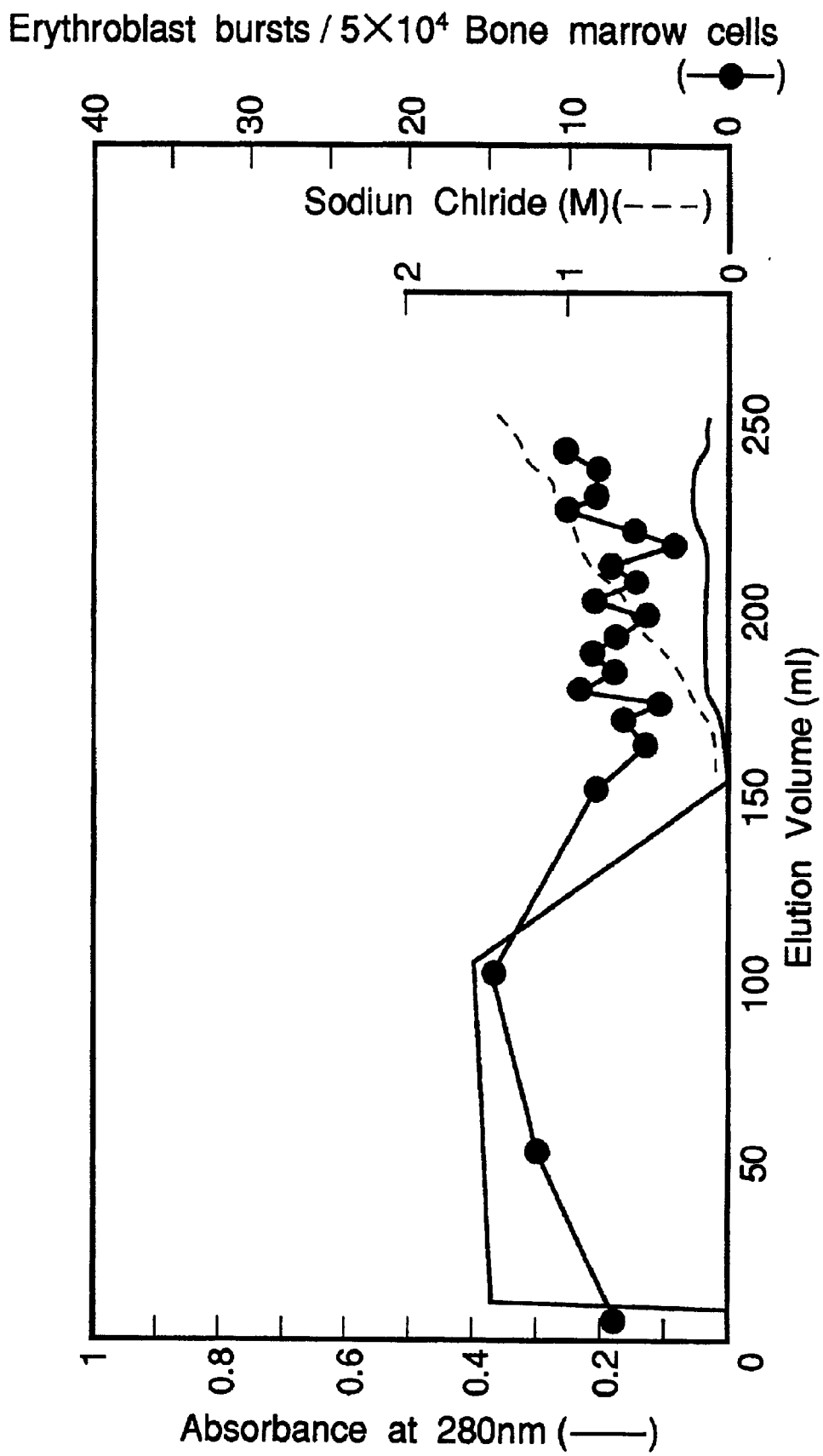
FIG. 14: a graph showing fractionation of the polypeptide of the invention through Blue-Sepharose.
Figure 15:
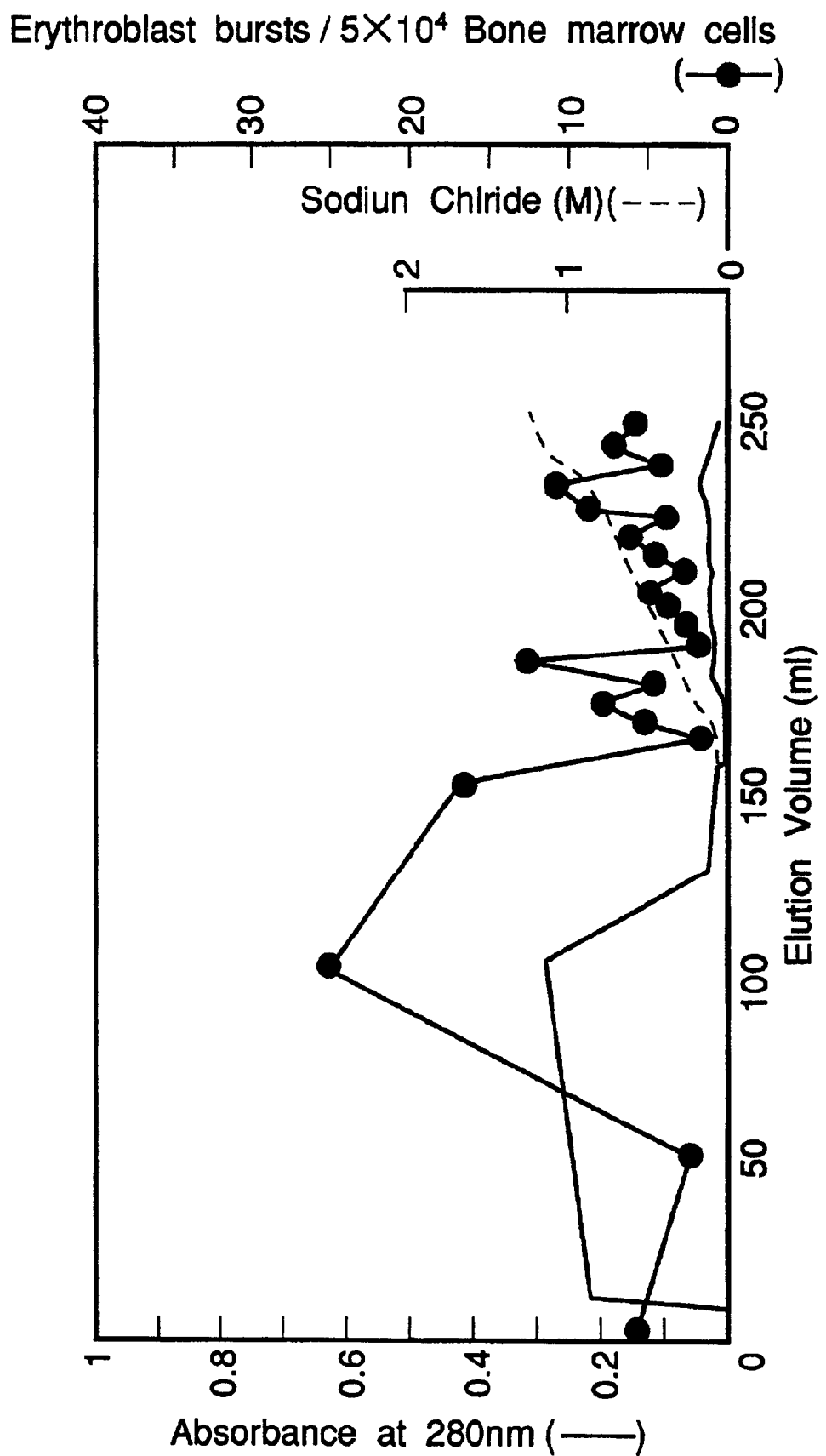
FIG. 15: a graph showing fractionation of the polypeptide of the invention through Red-Sepharose.
Figure 16:
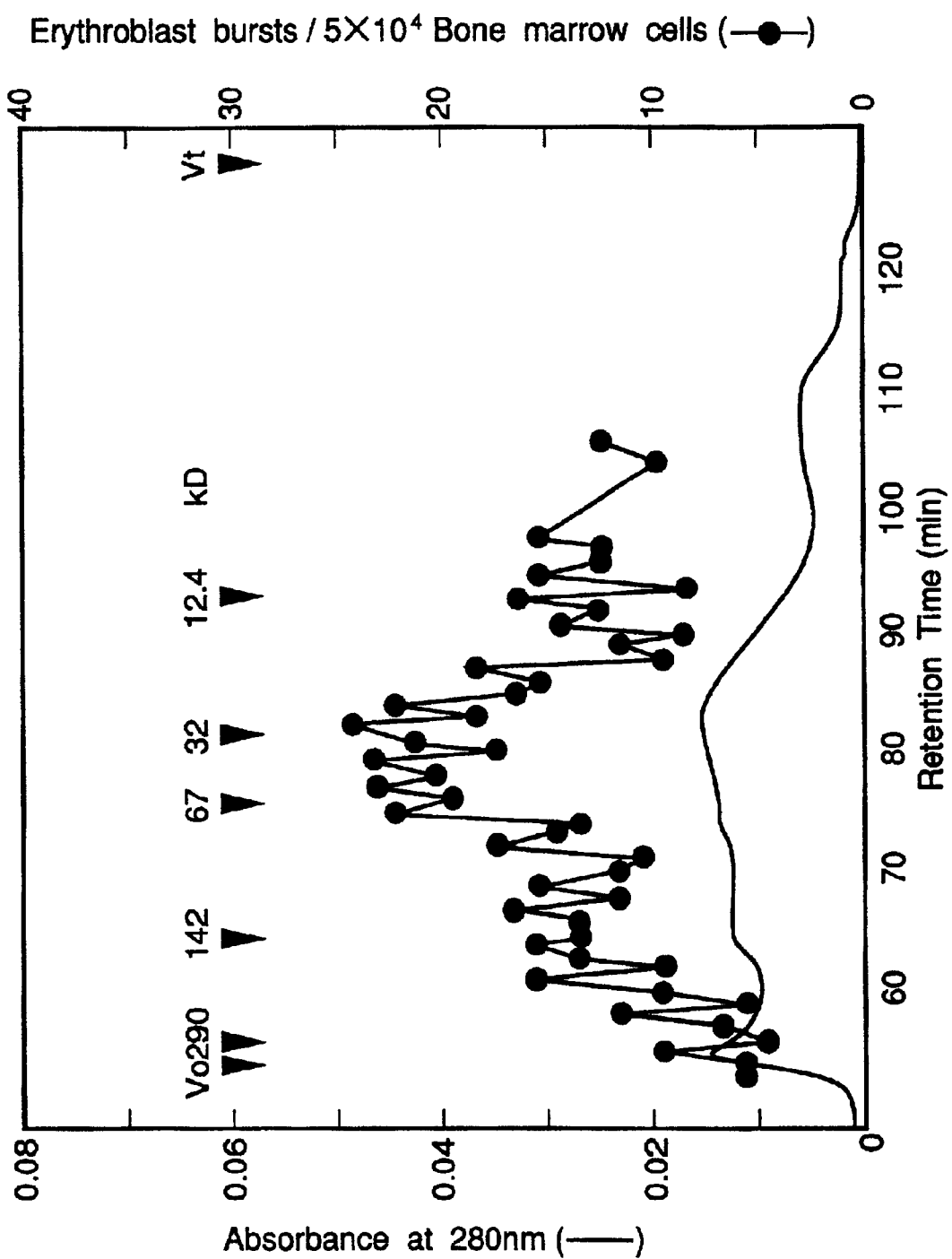
FIG. 16: a graph showing fractionation of the polypeptide of the invention through Sephacryl S-200HR.
Figure 17:
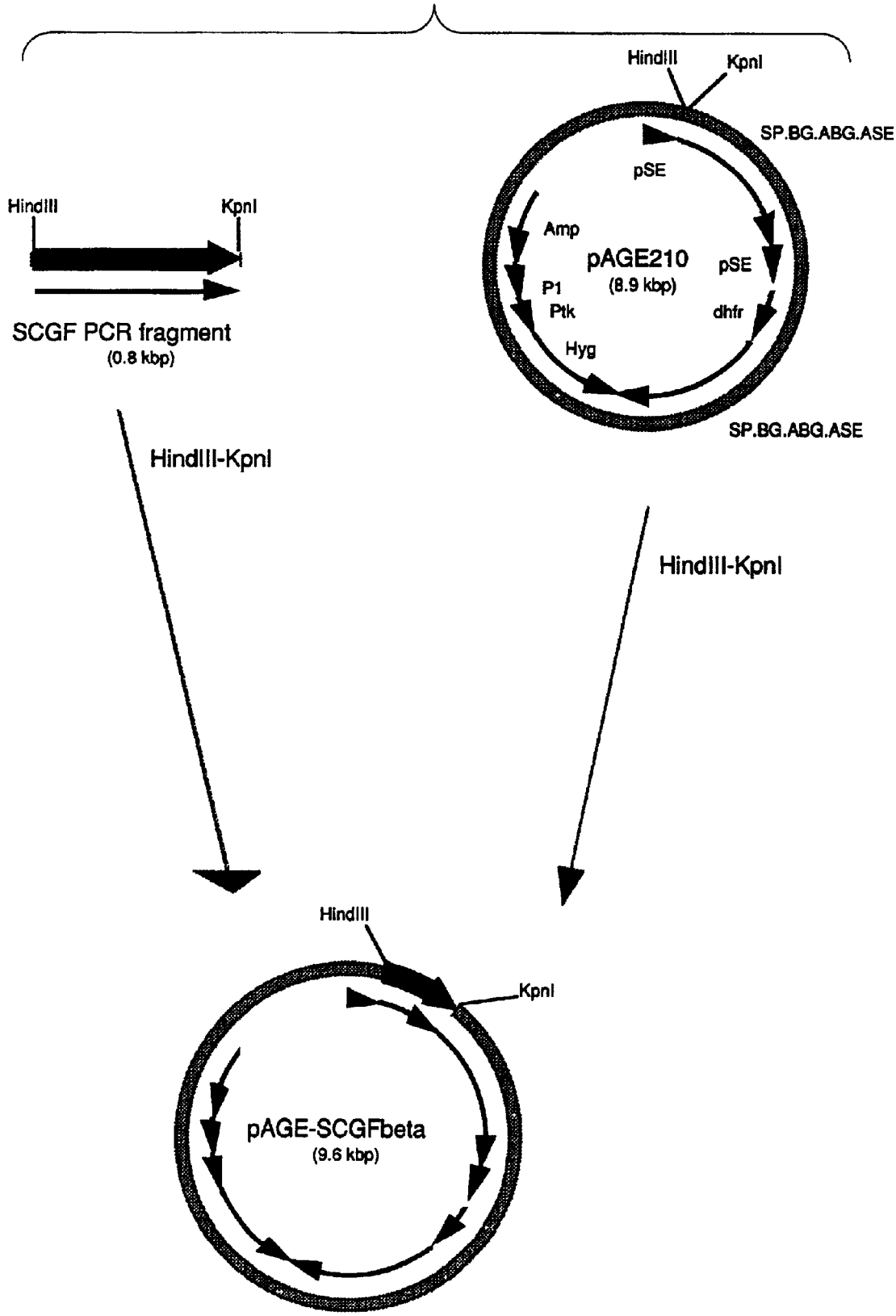
FIG. 17: a diagram illustrating the process for constructing pAGE-SCGFβ.
Figure 18:
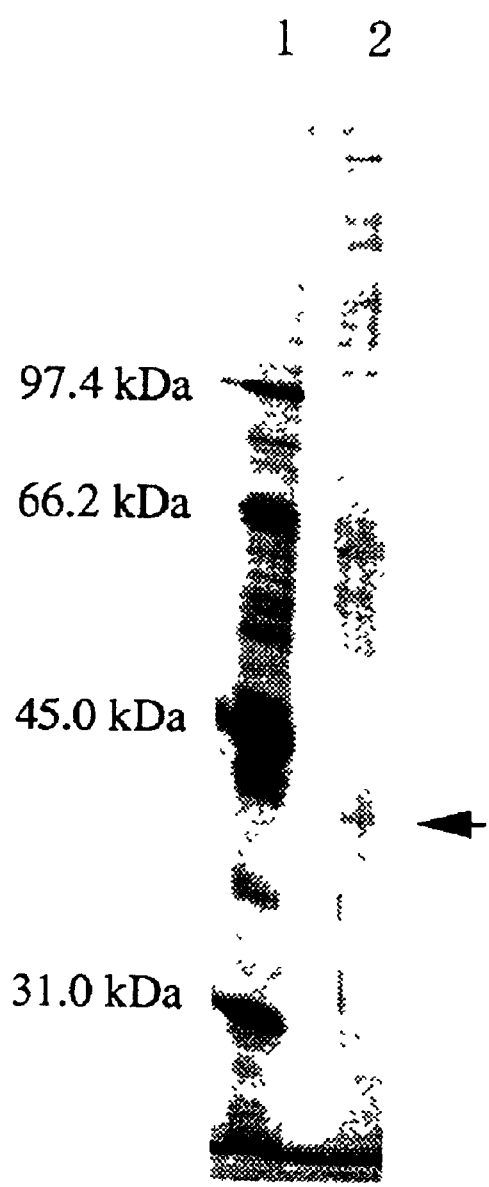
FIG. 18: SDS-PAGE pattern of a purified culture supernatant of CHO cells expressing human SCGF.

What is claimed is:

1. A purified hematopoietic stem cell growth factor polypeptide isolated from a mammal, which has erythroid burst-promoting activity and granulocyte macrophage colony-promoting activity on bone marrow cells of a human and which has a molecular weight of approximately 43 kDa by SDS-PAGE.

2. A purified hematopoietic stem cell growth factor polypeptide isolated from a mammal, which has erythroid burst-promoting activity and granulocyte macrophage colony-promoting activity on bone marrow cells of a mouse and which has a molecular weight of approximately 43 kDa by SDS-PAGE.

3. A purified hematopoietic stem cell growth factor polypeptide isolated from a mammal, which has erythroid burst-promoting activity and granulocyte macrophage colony-promoting activity on bone marrow cells of a rat and which has a molecular weight of approximately 43 kDa by SDS-PAGE.

4. A purified hematopoietic stem cell growth factor polypeptide isolated from a mammal, which comprises the amino acid residues from position 22 to position 245 of the amino acid sequence shown in SEQ ID NO: 1 or the amino acid residues from position 22 to position 323 of the amino acid sequence shown in SEQ ID NO: 4 and has erythroid burst-promoting activity and granulocyte macrophage colony-promoting activity on bone marrow cells of the mammal.

5. An isolated polypeptide comprising the amino acid sequence shown in SEQ ID NO: 1.

6. An isolated polypeptide comprising the amino acid sequence shown in SEQ ID NO: 4.

7. An isolated polypeptide comprising the amino acid sequence shown in SEQ ID NO: 8.

8. An isolated polypeptide comprising the amino acid sequence shown in SEQ ID NO: 12.

9. An isolated polynucleotide encoding the polypeptide of claim 4.

10. An isolated polynucleotide encoding the polypeptide of claim 5 or 6.

11. An isolated polynucleotide encoding the polypeptide of claim 7.

12. An isolated polynucleotide encoding the polypeptide of claim 8.

13. An isolated polynucleotide comprising the nucleotide sequence shown in SEQ ID NO: 2.

14. An isolated polynucleotide comprising the nucleotide sequence shown in SEQ ID NO: 5.

15. An isolated polynucleotide comprising the nucleotide sequence shown in SEQ ID NO: 9.

16. An isolated polynucleotide comprising the nucleotide sequence shown in SEQ ID NO: 13.

17. *Escherichia coli* SHDM11610C (FERM BP-5849) into which the isolated polynucleotide comprising the nucleotide sequence shown in SEQ ID NO: 2 is transferred.

18. *Escherichia coli* HSCGF (FERM BP-5986) into which the isolated polynucleotide comprising the nucleotide sequence shown in SEQ ID NO: 5 is transferred.

19. *Escherichia coli* MSCGF (FERM BP-5987) into which the isolated polynucleotide comprising the nucleotide sequence shown in SEQ ID NO: 9 is transferred.

20. *Escherichia coli* RSCGF (FERM BP-6063) into which the isolated polynucleotide comprising the nucleotide sequence shown in SEQ ID NO: 13 is transferred.

21. An isolated polynucleotide complementary to the isolated polynucleotide of claim 9.

22. An isolated polynucleotide complementary to the isolated polynucleotide of claim 10.

23. An isolated polynucleotide complementary to the isolated polynucleotide of claim 11.

24. An isolated polynucleotide complementary to the isolated polynucleotide of claim 12.

25. A vector comprising an isolated polynucleotide selected from:
   a) an isolated polynucleotide encoding a polypeptide having a sequence selected from SEQ ID NOS: 1, 4, 8, and 12;
   b) an isolated polynucleotide encoding a polypeptide having the amino acid sequence from 22 to 245 of SEQ ID NO: 1;
   c) an isolated polynucleotide encoding a polypeptide having the amino acid sequence from 22 to 323 of SEQ ID NO: 4;
   d) an isolated polynucleotide having a nucleotide sequence selected from SEQ ID NOS: 2, 5, 9, and 13; and
   e) an isolated polynucleotide complementary to the nucleotide sequence of (a), (b), (c), or (d).

26. A transformant obtained by introducing the vector of claim 25 into a host cell.

27. A method for producing a hematopoietic stem cell growth factor polypeptide having erythroid burst-promoting activity and granulocyte macrophage colony-promoting activity on bone marrow cells of a mammal, comprising culturing the transformant of claim 26 in a medium that promotes the production and accumulation of the polypeptide and recovering the polypeptide from the resultant culture.

28. The method of claim 27 further comprising the step of separating the polypeptide by using one or more carriers selected from an anion exchange carrier, a hydrophobic exchange group, a gel filtration carrier, an affinity carrier having a color exchange group, a lectin affinity carrier and a metal-chelating carrier.

29. A purified hematopoietic stem cell growth factor polypeptide isolated from a mammal, which has erythroid burst-promoting activity and granulocyte macrophage colony-promoting activity on bone marrow cells of the mammal and which has a molecular weight of approximately 43 kDa by SDS-PAGE.

30. The polypeptide of claim 29, wherein the polypeptide has erythroid burst-promoting activity and granulocyte macrophage colony-promoting activity on hematopoietic stem cells of the mammal.

31. A pharmaceutical composition comprising the polypeptide of claims 1 to 8, 30, or 29 as an active ingredient.

32. An antibody which reacts specifically with the polypeptide of claims 1 to 8, 30, or 29.

33. A microorganism, a non-human animal cell or a non-human animal which produces the antibody of claim 32.

* * * * *

UNITED STATES PATENT AND TRADEMARK OFFICE
CERTIFICATE OF CORRECTION

PATENT NO. : 6,541,217 B2
DATED : April 1, 2003
INVENTOR(S) : Hiraoka et al.

It is certified that error appears in the above-identified patent and that said Letters Patent is hereby corrected as shown below:

<u>Title page,</u>
Item [30], Foreign Application Priority Data, "PCT/JP99/2349" should read
-- PCT/JP97/2349 --.
Item [57], ABSTRACT,
Line 11, "in vitro" should read -- *in vitro* --.

Signed and Sealed this

Fifth Day of August, 2003

JAMES E. ROGAN
*Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 245 amino acids
      (B) TYPE: amino acid
      (D) TOPOLOGY: linear (ii) MOLECULE TYPE: protein (xi) SEQUENCE DESCRIPTION: SEQ ID NO:1:

```
Met Gln Ala Ala Trp Leu Leu Gly Ala Leu Val Val Pro Gln Leu Leu
 1               5                  10                  15

Gly Phe Gly His Gly Ala Arg Gly Ala Glu Arg Glu Trp Glu Gly Gly
            20                  25                  30
```

```
Trp Gly Gly Ala Gln Glu Glu Arg Glu Arg Glu Ala Leu Met Leu
         35                  40                  45

Lys His Leu Gln Glu Ala Leu Gly Leu Pro Ala Gly Arg Gly Asp Glu
 50                  55                  60

Asn Pro Ala Gly Thr Val Gly Lys Glu Asp Trp Glu Met Glu Glu
 65                  70                  75                  80

Asp Gln Gly Glu Glu Glu Glu Glu Ala Thr Pro Thr Pro Ser Ser
                 85                  90                  95

Gly Pro Ser Pro Ser Pro Thr Pro Glu Asp Ile Val Thr Tyr Ile Leu
             100                 105                 110

Gly Arg Leu Ala Gly Leu Asp Ala Gly Leu His Gln Leu His Val Arg
         115                 120                 125

Leu His Ala Leu Asp Thr Arg Val Val Glu Leu Thr Gln Gly Leu Arg
     130                 135                 140

Gln Leu Arg Asn Ala Ala Gly Asp Thr Arg Asp Ala Val Gln Ala Leu
145                 150                 155                 160

Gln Glu Ala Gln Gly Arg Ala Glu Arg Glu His Gly Arg Leu Glu Gly
                 165                 170                 175

Cys Leu Lys Gly Leu Arg Leu Gly His Lys Cys Phe Leu Leu Ser Arg
             180                 185                 190

Asp Phe Glu Ala Gln Pro Ser Ala Ser Pro His Pro Leu Ser Pro Asp
         195                 200                 205

Gln Pro Asn Gly Gly Thr Leu Glu Asn Cys Val Ala Gln Ala Ser Asp
     210                 215                 220

Asp Gly Ser Trp Trp Asp His Asp Cys Gln Arg Arg Leu Tyr Tyr Val
225                 230                 235                 240

Cys Glu Phe Pro Phe
                245

(2) INFORMATION FOR SEQ ID NO:2:

(i) SEQUENCE CHARACTERISTICS:
        (A) LENGTH: 1196 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens (ix) FEATURE:
        (A) NAME/KEY: CDS
        (B) LOCATION: 140..874

(xi) SEQUENCE DESCRIPTION: SEQ ID NO:2:

GAGAGAAGCT GGGAGAATCG GGAACCTGGG GGCTAGTGAC CTGCACACAG GGCAGGGGCA      60

CTCGGCAGTT CCCAGAGGCC ACCCCTCCCA CCCCAGACAT CCAGACATCT GGAACTTTGG     120

GTGCCAAGAG TCCAGCTTA ATG CAG GCA GCC TGG CTT TTG GGG GCT TTG GTG      172
                      Met Gln Ala Ala Trp Leu Leu Gly Ala Leu Val
                       1               5                  10

GTC CCC CAG CTC TTG GGC TTT GGC CAT GGG GCT CGG GGA GCA GAG AGG       220
Val Pro Gln Leu Leu Gly Phe Gly His Gly Ala Arg Gly Ala Glu Arg
             15                  20                  25

GAG TGG GAG GGA GGC TGG GGA GGT GCC CAG GAG GAG GAG CGG GAG AGG       268
Glu Trp Glu Gly Gly Trp Gly Gly Ala Gln Glu Glu Glu Arg Glu Arg
         30                  35                  40

GAG GCC CTG ATG CTG AAG CAT CTG CAG GAA GCC CTA GGA CTG CCT GCT       316
```

```
Glu Ala Leu Met Leu Lys His Leu Gln Glu Ala Leu Gly Leu Pro Ala
         45                  50                  55

GGG AGG GGG GAT GAG AAT CCT GCC GGA ACT GTT GAG GGA AAA GAG GAC         364
Gly Arg Gly Asp Glu Asn Pro Ala Gly Thr Val Glu Gly Lys Glu Asp
 60                  65                  70                  75

TGG GAG ATG GAG GAG GAC CAG GGG GAG GAA GAG GAG GAA GCA ACG             412
Trp Glu Met Glu Glu Asp Gln Gly Glu Glu Glu Glu Glu Ala Thr
                 80                  85                  90

CCA ACC CCA TCC TCC GGC CCC AGC CCC TCT CCC ACC CCT GAG GAC ATC         460
Pro Thr Pro Ser Ser Gly Pro Ser Pro Ser Pro Thr Pro Glu Asp Ile
                 95                 100                 105

GTC ACT TAC ATC CTG GGC CGC CTG GCC GGC CTG GAC GCA GGC CTG CAC         508
Val Thr Tyr Ile Leu Gly Arg Leu Ala Gly Leu Asp Ala Gly Leu His
            110                 115                 120

CAG CTG CAC GTC CGT CTG CAC GCG TTG GAC ACC CGC GTG GTC GAG CTG         556
Gln Leu His Val Arg Leu His Ala Leu Asp Thr Arg Val Val Glu Leu
            125                 130                 135

ACC CAG GGG CTG CGG CAG CTG CGG AAC GCG GCA GGC GAC ACC CGC GAT         604
Thr Gln Gly Leu Arg Gln Leu Arg Asn Ala Ala Gly Asp Thr Arg Asp
140                 145                 150                 155

GCC GTG CAA GCC CTG CAG GAG GCG CAG GGT CGC GCC GAG CGC GAG CAC         652
Ala Val Gln Ala Leu Gln Glu Ala Gln Gly Arg Ala Glu Arg Glu His
                160                 165                 170

GGC CGC TTG GAG GGC TGC CTG AAG GGG CTG CGC CTG GGC CAC AAG TGC         700
Gly Arg Leu Glu Gly Cys Leu Lys Gly Leu Arg Leu Gly His Lys Cys
                175                 180                 185

TTC CTG CTC TCG CGC GAC TTC GAA GCC CAG CCC AGC GCC TCG CCG CAT         748
Phe Leu Leu Ser Arg Asp Phe Glu Ala Gln Pro Ser Ala Ser Pro His
            190                 195                 200

CCG CTC AGC CCG GAC CAG CCC AAC GGT GGC ACG CTC GAG AAC TGC GTG         796
Pro Leu Ser Pro Asp Gln Pro Asn Gly Gly Thr Leu Glu Asn Cys Val
            205                 210                 215

GCG CAG GCC TCT GAC GAC GGC TCC TGG TGG GAC CAC GAC TGC CAG CGG         844
Ala Gln Ala Ser Asp Asp Gly Ser Trp Trp Asp His Asp Cys Gln Arg
220                 225                 230                 235

CGT CTC TAC TAC GTC TGC GAG TTC CCC TTC TAGCGGGGCC GGTACCCCGC           894
Arg Leu Tyr Tyr Val Cys Glu Phe Pro Phe
                240                 245

CTCCCTGCCC ATCCCACCAC CCGGCCTTTC CCTGCGCCGT GCCCACCCTC CTCCGGAATC       954

TCCCTTCCCT TCCTGGCCAC GAATGGCAGC GTCCTCCCCG ACCCCAGTC TGGGCGCTTC       1014

TGGGAGGGCT CTTGCGGTGC CGGCACTCCT CCTTGTTAGT GTCTTTCCTT GAAGGGGCGG      1074

GCACCAGGCC AGGTCCGGTG CCAATAAATC CTTGTGGAAT CTGACTTGAG GGCAAAAAA       1134

AAAAAAAAAA AAAAAAAAAA AAAAAAAAAA AAAAAAAAAA AAAAAAAAAA AAAAAAAAAA      1194

AA                                                                     1196

(2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:3:

GATATCTTCC AGTTTGGAAC AAGAGTCCAC TATTAAAGAA CGTGG                        45
```

(2) INFORMATION FOR SEQ ID NO:4:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gln Ala Ala Trp Leu Leu Gly Ala Leu Val Val Pro Gln Leu Leu
 1               5                  10                  15

Gly Phe Gly His Gly Ala Arg Gly Ala Glu Arg Glu Trp Glu Gly Gly
            20                  25                  30

Trp Gly Gly Ala Gln Glu Glu Glu Arg Glu Arg Glu Ala Leu Met Leu
            35                  40                  45

Lys His Leu Gln Glu Ala Leu Gly Leu Pro Ala Gly Arg Gly Asp Glu
    50                  55                  60

Asn Pro Ala Gly Thr Val Glu Gly Lys Glu Asp Trp Glu Met Glu Glu
 65                  70                  75                  80

Asp Gln Gly Glu Glu Glu Glu Glu Ala Thr Pro Thr Pro Ser Ser
            85                  90                  95

Gly Pro Ser Pro Ser Pro Thr Pro Glu Asp Ile Val Thr Tyr Ile Leu
            100                 105                 110

Gly Arg Leu Ala Gly Leu Asp Ala Gly Leu His Gln Leu His Val Arg
            115                 120                 125

Leu His Ala Leu Asp Thr Arg Val Val Glu Leu Thr Gln Gly Leu Arg
    130                 135                 140

Gln Leu Arg Asn Ala Ala Gly Asp Thr Arg Asp Ala Val Gln Ala Leu
145                 150                 155                 160

Gln Glu Ala Gln Gly Arg Ala Glu Arg Glu His Gly Arg Leu Glu Gly
            165                 170                 175

Cys Leu Lys Gly Leu Arg Leu Gly His Lys Cys Phe Leu Leu Ser Arg
            180                 185                 190

Asp Phe Glu Ala Gln Ala Ala Ala Gln Ala Arg Cys Thr Ala Arg Gly
    195                 200                 205

Gly Ser Leu Ala Gln Pro Ala Asp Arg Gln Gln Met Glu Ala Leu Thr
    210                 215                 220

Arg Tyr Leu Arg Ala Ala Leu Ala Pro Tyr Asn Trp Pro Val Trp Leu
225                 230                 235                 240

Gly Val His Asp Arg Arg Ala Glu Gly Leu Tyr Leu Phe Glu Asn Gly
            245                 250                 255

Gln Arg Val Ser Phe Phe Ala Trp His Arg Ser Pro Arg Pro Glu Leu
            260                 265                 270

Gly Ala Gln Pro Ser Ala Ser Pro His Pro Leu Ser Pro Asp Gln Pro
            275                 280                 285

Asn Gly Gly Thr Leu Glu Asn Cys Val Ala Gln Ala Ser Asp Gly
    290                 295                 300

Ser Trp Trp Asp His Asp Cys Gln Arg Arg Leu Tyr Tyr Val Cys Glu
305                 310                 315                 320

Phe Pro Phe
```

(2) INFORMATION FOR SEQ ID NO:5:

(i) SEQUENCE CHARACTERISTICS:
        (A) LENGTH: 969 base pairs (B) TYPE: nucleic acid
(C) STRANDEDNESS: single
(D) TOPOLOGY: linear (ii) MOLECULE TYPE: cDNA to mRNA (vi) ORIGINAL SOURCE:
(A) ORGANISM: Homo sapiens (ix) FEATURE:
(A) NAME/KEY: CDS
(B) LOCATION: 1..969

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | CAG | GCA | GCC | TGG | CTT | TTG | GGG | GCT | TTG | GTG | GTC | CCC | CAG | CTC | TTG | 48 |
| Met | Gln | Ala | Ala | Trp | Leu | Leu | Gly | Ala | Leu | Val | Val | Pro | Gln | Leu | Leu | |
| 1 | | | | 5 | | | | | 10 | | | | | 15 | | |
| GGC | TTT | GGC | CAT | GGG | GCT | CGG | GGA | GCA | GAG | AGG | GAG | TGG | GAG | GGA | GGC | 96 |
| Gly | Phe | Gly | His | Gly | Ala | Arg | Gly | Ala | Glu | Arg | Glu | Trp | Glu | Gly | Gly | |
| | | | 20 | | | | | 25 | | | | | 30 | | | |
| TGG | GGA | GGT | GCC | CAG | GAG | GAG | GAG | CGG | GAG | AGG | GAG | GCC | CTG | ATG | CTG | 144 |
| Trp | Gly | Gly | Ala | Gln | Glu | Glu | Glu | Arg | Glu | Arg | Glu | Ala | Leu | Met | Leu | |
| | | 35 | | | | | 40 | | | | | 45 | | | | |
| AAG | CAT | CTG | CAG | GAA | GCC | CTA | GGA | CTG | CCT | GCT | GGG | AGG | GGG | GAT | GAG | 192 |
| Lys | His | Leu | Gln | Glu | Ala | Leu | Gly | Leu | Pro | Ala | Gly | Arg | Gly | Asp | Glu | |
| | 50 | | | | | 55 | | | | | 60 | | | | | |
| AAT | CCT | GCC | GGA | ACT | GTT | GAG | GGA | AAA | GAG | GAC | TGG | GAG | ATG | GAG | GAG | 240 |
| Asn | Pro | Ala | Gly | Thr | Val | Glu | Gly | Lys | Glu | Asp | Trp | Glu | Met | Glu | Glu | |
| 65 | | | | 70 | | | | | 75 | | | | | 80 | | |
| GAC | CAG | GGG | GAG | GAA | GAG | GAG | GAG | GAA | GCA | ACG | CCA | ACC | CCA | TCC | TCC | 288 |
| Asp | Gln | Gly | Glu | Glu | Glu | Glu | Glu | Glu | Ala | Thr | Pro | Thr | Pro | Ser | Ser | |
| | | | 85 | | | | | 90 | | | | | 95 | | | |
| GGC | CCC | AGC | CCC | TCT | CCC | ACC | CCT | GAG | GAC | ATC | GTC | ACT | TAC | ATC | CTG | 336 |
| Gly | Pro | Ser | Pro | Ser | Pro | Thr | Pro | Glu | Asp | Ile | Val | Thr | Tyr | Ile | Leu | |
| | | | 100 | | | | | 105 | | | | | 110 | | | |
| GGC | CGC | CTG | GCC | GGC | CTG | GAC | GCA | GGC | CTG | CAC | CAG | CTG | CAC | GTC | CGT | 384 |
| Gly | Arg | Leu | Ala | Gly | Leu | Asp | Ala | Gly | Leu | His | Gln | Leu | His | Val | Arg | |
| | | 115 | | | | | 120 | | | | | 125 | | | | |
| CTG | CAC | GCG | TTG | GAC | ACC | CGC | GTG | GTC | GAG | CTG | ACC | CAG | GGG | CTG | CGG | 432 |
| Leu | His | Ala | Leu | Asp | Thr | Arg | Val | Val | Glu | Leu | Thr | Gln | Gly | Leu | Arg | |
| | 130 | | | | | 135 | | | | | 140 | | | | | |
| CAG | CTG | CGG | AAC | GCG | GCA | GGC | GAC | ACC | CGC | GAT | GCC | GTG | CAA | GCC | CTG | 480 |
| Gln | Leu | Arg | Asn | Ala | Ala | Gly | Asp | Thr | Arg | Asp | Ala | Val | Gln | Ala | Leu | |
| 145 | | | | 150 | | | | | 155 | | | | | 160 | | |
| CAG | GAG | GCG | CAG | GGT | CGC | GCC | GAG | CGC | GAG | CAC | GGC | CGC | TTG | GAG | GGC | 528 |
| Gln | Glu | Ala | Gln | Gly | Arg | Ala | Glu | Arg | Glu | His | Gly | Arg | Leu | Glu | Gly | |
| | | | 165 | | | | | 170 | | | | | 175 | | | |
| TGC | CTG | AAG | GGG | CTG | CGC | CTG | GGC | CAC | AAG | TGC | TTC | CTG | CTC | TCG | CGC | 576 |
| Cys | Leu | Lys | Gly | Leu | Arg | Leu | Gly | His | Lys | Cys | Phe | Leu | Leu | Ser | Arg | |
| | | 180 | | | | | 185 | | | | | 190 | | | | |
| GAC | TTC | GAA | GCT | CAG | GCG | GCG | GCG | CAG | GCG | CGG | TGC | ACG | GCG | CGG | GGC | 624 |
| Asp | Phe | Glu | Ala | Gln | Ala | Ala | Ala | Gln | Ala | Arg | Cys | Thr | Ala | Arg | Gly | |
| | 195 | | | | | 200 | | | | | 205 | | | | | |
| GGG | AGC | CTG | GCG | CAG | CCG | GCA | GAC | CGC | CAG | CAG | ATG | GAG | GCG | CTC | ACT | 672 |
| Gly | Ser | Leu | Ala | Gln | Pro | Ala | Asp | Arg | Gln | Gln | Met | Glu | Ala | Leu | Thr | |
| | | | 210 | | | | | 215 | | | | | 220 | | | |
| CGG | TAC | CTG | CGC | GCG | GCG | CTC | GCT | CCC | TAC | AAC | TGG | CCC | GTG | TGG | CTG | 720 |
| Arg | Tyr | Leu | Arg | Ala | Ala | Leu | Ala | Pro | Tyr | Asn | Trp | Pro | Val | Trp | Leu | |
| 225 | | | | 230 | | | | | 235 | | | | | 240 | | |
| GGC | GTG | CAC | GAT | CGG | CGC | GCC | GAG | GGC | CTC | TAC | CTC | TTC | GAA | AAC | GGC | 768 |
| Gly | Val | His | Asp | Arg | Arg | Ala | Glu | Gly | Leu | Tyr | Leu | Phe | Glu | Asn | Gly | |
| | | | 245 | | | | | 250 | | | | | 255 | | | |

-continued

```
CAG CGC GTG TCC TTC TTC GCC TGG CAT CGC TCA CCC CGC CCC GAG CTC     816
Gln Arg Val Ser Phe Phe Ala Trp His Arg Ser Pro Arg Pro Glu Leu
        260                 265                 270

GGC GCC CAG CCC AGC GCC TCG CCG CAT CCG CTC AGC CCG GAC CAG CCC     864
Gly Ala Gln Pro Ser Ala Ser Pro His Pro Leu Ser Pro Asp Gln Pro
            275                 280                 285

AAC GGT GGC ACG CTC GAG AAC TGC GTG GCG CAG GCC TCT GAC GAC GGC     912
Asn Gly Gly Thr Leu Glu Asn Cys Val Ala Gln Ala Ser Asp Asp Gly
290                 295                 300

TCC TGG TGG GAC CAC GAC TGC CAG CGG CGT CTC TAC TAC GTC TGC GAG     960
Ser Trp Trp Asp His Asp Cys Gln Arg Arg Leu Tyr Tyr Val Cys Glu
305                 310                 315                 320

TTC CCC TTC                                                         969
Phe Pro Phe
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

```
GAGTCCAGCT TAATGCAGGC A                                              21
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

```
CTAGAAGGGG AACTCGCAGA C                                              21
```

(2) INFORMATION FOR SEQ ID NO:8:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Ala Ala Trp Leu Leu Gly Ala Leu Val Val Pro Gln Leu Leu
1               5                   10                  15

Ser Phe Gly His Gly Ala Arg Gly Pro Gly Arg Glu Trp Glu Gly Gly
            20                  25                  30

Trp Gly Gly Ala Leu Glu Glu Glu Arg Glu Arg Glu Ser Gln Met Leu
        35                  40                  45

Lys Asn Leu Gln Glu Ala Leu Gly Leu Pro Thr Gly Val Gly Asn Glu
    50                  55                  60

Asp Asn Leu Ala Glu Asn Pro Glu Asp Lys Glu Val Trp Glu Thr Thr
65                  70                  75                  80
```

```
Glu Thr Gln Gly Glu Glu Glu Glu Ile Thr Thr Ala Pro Ser
            85                  90                  95

Ser Ser Pro Asn Pro Phe Pro Ser Pro Ser Pro Thr Pro Glu Asp Thr
            100                 105                 110

Val Thr Tyr Ile Leu Gly Arg Leu Ala Ser Leu Asp Ala Gly Leu His
            115                 120                 125

Gln Leu His Val Arg Leu His Val Leu Asp Thr Arg Val Val Glu Leu
    130                 135                 140

Thr Gln Gly Leu Arg Gln Leu Arg Asp Ala Ala Ser Asp Thr Arg Asp
145                 150                 155                 160

Ser Val Gln Ala Leu Lys Glu Val Gln Asp Arg Ala Glu Gln Glu His
                165                 170                 175

Gly Arg Leu Glu Gly Cys Leu Lys Gly Leu Arg Leu Gly His Lys Cys
            180                 185                 190

Phe Leu Leu Ser Arg Asp Phe Glu Thr Gln Ala Ala Ala Gln Ala Arg
            195                 200                 205

Cys Lys Ala Arg Gly Gly Ser Leu Ala Gln Pro Ala Asp Arg Gln Gln
    210                 215                 220

Met Asp Ala Leu Ser Arg Tyr Leu Arg Ala Ala Leu Ala Pro Tyr Asn
225                 230                 235                 240

Trp Pro Val Trp Leu Gly Val His Asp Arg Arg Ser Glu Gly Leu Tyr
                245                 250                 255

Leu Phe Glu Asn Gly Gln Arg Val Ser Phe Phe Ala Trp His Arg Ala
            260                 265                 270

Phe Ser Leu Glu Ser Gly Ala Gln Pro Ser Ala Ala Thr His Pro Leu
            275                 280                 285

Ser Pro Asp Gln Pro Asn Gly Gly Val Leu Glu Asn Cys Val Ala Gln
    290                 295                 300

Ala Ser Asp Asp Gly Ser Trp Trp Asp His Asp Cys Glu Arg Arg Leu
305                 310                 315                 320

Tyr Phe Val Cys Glu Phe Pro Phe
                325

(2) INFORMATION FOR SEQ ID NO:9:

(i) SEQUENCE CHARACTERISTICS:
        (A) LENGTH: 1399 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: mouse (ix) FEATURE:
        (A) NAME/KEY: CDS
        (B) LOCATION: 132..1115

(xi) SEQUENCE DESCRIPTION: SEQ ID NO:9:

GAAGCTGGCA GAAGAAGGTC AAGGGGCTTG TGAGCTGCCC ACCAGACTGG GACACTTGCT      60

AGGTCTATAC AGCAGTCCTA CCCCTGGCAT TCTGACCTCT CTACTATTTG GGTGCTGGGA     120

AGCCCAGCTG G ATG CAG GCA GCC TGG CTC TTG GGG GCC CTA GTG GTC CCT     170
             Met Gln Ala Ala Trp Leu Leu Gly Ala Leu Val Val Pro
               1               5                  10

CAG CTT TTG AGT TTT GGT CAT GGA GCC CGA GGT CCT GGG AGG GAG TGG      218
Gln Leu Leu Ser Phe Gly His Gly Ala Arg Gly Pro Gly Arg Glu Trp
     15                  20                  25
```

```
GAG GGA GGC TGG GGA GGT GCC CTG GAG GAG GAG AGA GAG CGG GAG TCA      266
Glu Gly Gly Trp Gly Gly Ala Leu Glu Glu Glu Arg Glu Arg Glu Ser
 30              35                  40                  45

CAG ATG TTG AAG AAT CTC CAG GAG GCC CTA GGG CTG CCC ACT GGG GTG      314
Gln Met Leu Lys Asn Leu Gln Glu Ala Leu Gly Leu Pro Thr Gly Val
                 50                  55                  60

GGA AAT GAG GAT AAT CTT GCT GAA AAC CCT GAA GAC AAA GAG GTC TGG      362
Gly Asn Glu Asp Asn Leu Ala Glu Asn Pro Glu Asp Lys Glu Val Trp
             65                  70                  75

GAG ACC ACA GAG ACT CAA GGG GAA GAA GAG GAA GAG GAA ATC ACC ACA      410
Glu Thr Thr Glu Thr Gln Gly Glu Glu Glu Glu Glu Glu Ile Thr Thr
         80                  85                  90

GCA CCT TCT TCT AGT CCC AAC CCT TTC CCC AGC CCT TCT CCC ACA CCA      458
Ala Pro Ser Ser Ser Pro Asn Pro Phe Pro Ser Pro Ser Pro Thr Pro
     95                  100                 105

GAG GAC ACT GTC ACT TAC ATC TTG GGC CGC TTG GCC AGC CTC GAT GCA      506
Glu Asp Thr Val Thr Tyr Ile Leu Gly Arg Leu Ala Ser Leu Asp Ala
110                 115                 120                 125

GGC CTA CAC CAA TTG CAC GTC CGT CTG CAC GTT TTG GAC ACC CGT GTG      554
Gly Leu His Gln Leu His Val Arg Leu His Val Leu Asp Thr Arg Val
                130                 135                 140

GTT GAG CTG ACC CAG GGG CTG CGG CAG CTG CGG GAT GCT GCG AGT GAC      602
Val Glu Leu Thr Gln Gly Leu Arg Gln Leu Arg Asp Ala Ala Ser Asp
            145                 150                 155

ACC CGC GAC TCA GTG CAA GCC CTG AAG GAG GTC CAG GAC CGT GCT GAG      650
Thr Arg Asp Ser Val Gln Ala Leu Lys Glu Val Gln Asp Arg Ala Glu
        160                 165                 170

CAG GAG CAC GGC CGC TTG GAG GGC TGC CTG AAG GGC CTG CGC CTT GGC      698
Gln Glu His Gly Arg Leu Glu Gly Cys Leu Lys Gly Leu Arg Leu Gly
    175                 180                 185

CAC AAG TGC TTC CTG CTC TCG CGA GAC TTC GAG ACC CAG GCG GCG GCG      746
His Lys Cys Phe Leu Leu Ser Arg Asp Phe Glu Thr Gln Ala Ala Ala
190                 195                 200                 205

CAG GCG CGG TGC AAG GCG CGA GGT GGG AGC TTA GCA CAG CCT GCG GAC      794
Gln Ala Arg Cys Lys Ala Arg Gly Gly Ser Leu Ala Gln Pro Ala Asp
                210                 215                 220

CGC CAG CAA ATG GAT GCG CTA AGC CGG TAC TTA CGC GCC GCT CTC GCC      842
Arg Gln Gln Met Asp Ala Leu Ser Arg Tyr Leu Arg Ala Ala Leu Ala
            225                 230                 235

CCC TAC AAC TGG CCG GTG TGG CTG GGA GTG CAC GAT CGG CGC TCC GAG      890
Pro Tyr Asn Trp Pro Val Trp Leu Gly Val His Asp Arg Arg Ser Glu
        240                 245                 250

GGG CTC TAC CTT TTC GAG AAC GGC CAG CGC GTG TCT TTC TTC GCC TGG      938
Gly Leu Tyr Leu Phe Glu Asn Gly Gln Arg Val Ser Phe Phe Ala Trp
    255                 260                 265

CAC CGC GCA TTC AGC CTG GAG TCC GGC GCC CAG CCT AGT GCG GCA ACA      986
His Arg Ala Phe Ser Leu Glu Ser Gly Ala Gln Pro Ser Ala Ala Thr
270                 275                 280                 285

CAT CCA CTC AGC CCG GAT CAG CCC AAT GGC GGC GTC CTG GAG AAC TGC     1034
His Pro Leu Ser Pro Asp Gln Pro Asn Gly Gly Val Leu Glu Asn Cys
                290                 295                 300

GTG GCC CAG GCC TCA GAC GAC GGT TCT TGG TGG GAC CAT GAC TGT GAG     1082
Val Ala Gln Ala Ser Asp Asp Gly Ser Trp Trp Asp His Asp Cys Glu
            305                 310                 315

CGG CGC CTC TAC TTC GTC TGC GAG TTC CCC TTC TAGAGAACCG GTCTCTGCCC   1135
Arg Arg Leu Tyr Phe Val Cys Glu Phe Pro Phe
        320                 325

AGGAGCTCTA GTGCACATTT TGCACCGTAC ACCGCGCACC CTATTGTTAG GGGCCTGGGA   1195
```

```
GTCGCTCAGA GATTAAGCGT GACCATGAAT ACATTTTAAT CAGAAGAGGT TTTTTATTTT    1255

AGATACTGGC ACCCAGACTG ATTGGGGCCA GGTGTGCTCC TGAGATTGCT TCCAAGATGC    1315

ATTATCAGCC CAGGGATTTT AAAGGCAAAC CCCACAAGAT TGCATGTAGC CTGCTTACAT    1375

GTAGGCCGGA GCATAAAAAT TTAA                                          1399
```

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:10:

```
CTTTAGAGCA C                                                           11
```

(2) INFORMATION FOR SEQ ID NO:11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:11:

```
CTCTAAAG                                                                8
```

(2) INFORMATION FOR SEQ ID NO:12:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gln Ala Ala Trp Leu Leu Gly Ala Leu Leu Val Pro His Leu Leu
 1               5                  10                  15

Ser Phe Gly His Gly Ala Arg Gly His Gly Lys Glu Trp Glu Gly Val
            20                  25                  30

Trp Gly Gly Ala Leu Glu Glu Glu Arg Asp Arg Glu Ser Leu Met Leu
        35                  40                  45

Lys Asn Leu Gln Glu Ala Leu Gly Leu Pro Thr Gly Val Gly Asn Lys
    50                  55                  60

Asp Asn Leu Ala Glu Asn Ser Glu Gly Lys Glu Val Trp Glu Ala Thr
65                  70                  75                  80

Glu Thr Gln Gly Glu Glu Glu Glu Glu Thr Thr Thr Thr Pro Ser
                85                  90                  95

Ser Ser Pro Thr Pro Phe Pro Ser Pro Ser Pro Thr Ser Glu Asp Thr
            100                 105                 110

Val Thr Tyr Ile Leu Gly Arg Leu Ala Ser Leu Asp Ala Gly Leu His
        115                 120                 125

Gln Leu His Ile Arg Leu His Val Leu Asp Thr Arg Val Val Glu Leu
    130                 135                 140
```

```
Thr Gln Gly Leu Arg Arg Leu Arg Asp Ala Ala Ser Asp Thr Arg Asp
145                 150                 155                 160

Ser Val Gln Ala Leu Lys Glu Val Gln Val Arg Ser Glu Gln Glu His
                165                 170                 175

Gly Arg Leu Glu Gly Cys Leu Lys Gly Leu Arg Leu Gly His Lys Cys
            180                 185                 190

Phe Leu Leu Ser Arg Asp Phe Glu Thr Gln Ala Ala Gln Ala Arg
            195                 200                 205

Cys Lys Ala Arg Gly Gly Ser Leu Ala Gln Pro Ala Asp Arg Gln Gln
    210                 215                 220

Met Asp Ala Leu Ser Arg Tyr Leu Arg Ala Ala Leu Ala Pro Tyr Asn
225                 230                 235                 240

Trp Pro Val Trp Leu Gly Val His Asp Arg Ser Glu Gly Leu Tyr
                245                 250                 255

Leu Phe Glu Asn Gly Gln Arg Val Ser Phe Phe Ala Trp His Arg Ala
            260                 265                 270

Leu Ser Pro Glu Ser Gly Ala Gln Pro Ser Ala Ala Ser His Pro Leu
            275                 280                 285

Ser Pro Asp Gln Pro Asn Gly Gly Ile Leu Glu Asn Cys Val Ala Gln
    290                 295                 300

Ala Ser Asp Asp Gly Ser Trp Trp Asp His Asp Cys Glu Arg Arg Leu
305                 310                 315                 320

Tyr Phe Val Cys Glu Phe Pro Phe
                325
```

(2) INFORMATION FOR SEQ ID NO:13:

(i) SEQUENCE CHARACTERISTICS:
        (A) LENGTH: 984 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: rat (ix) FEATURE:
        (A) NAME/KEY: CDS
        (B) LOCATION: 1..984

(xi) SEQUENCE DESCRIPTION: SEQ ID NO:13:

```
ATG CAG GCA GCC TGG CTC TTG GGG GCC CTA CTG GTC CCT CAC CTT TTG        48
Met Gln Ala Ala Trp Leu Leu Gly Ala Leu Leu Val Pro His Leu Leu
  1               5                  10                  15

AGT TTT GGC CAT GGA GCC CGA GGT CAT GGG AAG GAA TGG GAA GGA GTC        96
Ser Phe Gly His Gly Ala Arg Gly His Gly Lys Glu Trp Glu Gly Val
                 20                  25                  30

TGG GGA GGT GCC CTG GAG GAG GAG CGA GAT CGG GAG TCA CTG ATG TTG       144
Trp Gly Gly Ala Leu Glu Glu Glu Arg Asp Arg Glu Ser Leu Met Leu
         35                  40                  45

AAG AAT CTC CAG GAG GCC CTA GGG CTG CCC ACT GGG GTG GGA AAT AAG       192
Lys Asn Leu Gln Glu Ala Leu Gly Leu Pro Thr Gly Val Gly Asn Lys
     50                  55                  60

GAT AAT CTT GCT GAA AAC TCT GAA GGC AAA GAG GTC TGG GAG GCC ACG       240
Asp Asn Leu Ala Glu Asn Ser Glu Gly Lys Glu Val Trp Glu Ala Thr
 65                  70                  75                  80

GAG ACT CAA GGG GAA GAA GAG GAA GAG GAA ACC ACC ACA ACA CCT TCT       288
Glu Thr Gln Gly Glu Glu Glu Glu Glu Thr Thr Thr Thr Pro Ser
                 85                  90                  95
```

```
TCT AGC CCC ACT CCT TTC CCC AGC CCT TCT CCT ACA TCA GAG GAC ACA    336
Ser Ser Pro Thr Pro Phe Pro Ser Pro Ser Pro Thr Ser Glu Asp Thr
            100                 105                 110

GTC ACT TAC ATC CTG GGC CGC TTG GCC AGC CTC GAT GCA GGC CTA CAC    384
Val Thr Tyr Ile Leu Gly Arg Leu Ala Ser Leu Asp Ala Gly Leu His
            115                 120                 125

CAA TTG CAC ATC CGT CTG CAT GTT TTG GAC ACC CGT GTG GTT GAG CTG    432
Gln Leu His Ile Arg Leu His Val Leu Asp Thr Arg Val Val Glu Leu
            130                 135                 140

ACC CAG GGG CTG CGG CGG CTG CGG GAT GCC GCG AGT GAC ACC CGC GAC    480
Thr Gln Gly Leu Arg Arg Leu Arg Asp Ala Ala Ser Asp Thr Arg Asp
145                 150                 155                 160

TCA GTG CAA GCT CTG AAG GAG GTA CAG GTC CGT TCT GAG CAG GAG CAC    528
Ser Val Gln Ala Leu Lys Glu Val Gln Val Arg Ser Glu Gln Glu His
            165                 170                 175

GGC CGC TTG GAG GGC TGC CTG AAG GGC CTG CGC CTA GGC CAC AAA TGC    576
Gly Arg Leu Glu Gly Cys Leu Lys Gly Leu Arg Leu Gly His Lys Cys
            180                 185                 190

TTC CTG CTC TCG CGA GAC TTC GAG ACA CAG GCG GCG GCG CAA GCG CGG    624
Phe Leu Leu Ser Arg Asp Phe Glu Thr Gln Ala Ala Ala Gln Ala Arg
            195                 200                 205

TGT AAG GCG CGA GGT GGG AGT TTA GCG CAG CCT GCG GAC CGC CAG CAA    672
Cys Lys Ala Arg Gly Gly Ser Leu Ala Gln Pro Ala Asp Arg Gln Gln
210                 215                 220

ATG GAT GCT CTA AGC CGG TAC TTA CGA GCT GCT CTT GCC CCC TAC AAC    720
Met Asp Ala Leu Ser Arg Tyr Leu Arg Ala Ala Leu Ala Pro Tyr Asn
225                 230                 235                 240

TGG CCA GTG TGG CTG GGA GTG CAC GAC CGG CGC TCG GAG GGG CTC TAC    768
Trp Pro Val Trp Leu Gly Val His Asp Arg Arg Ser Glu Gly Leu Tyr
            245                 250                 255

CTT TTC GAG AAC GGC CAG CGC GTG TCA TTC TTC GCC TGG CAC CGC GCA    816
Leu Phe Glu Asn Gly Gln Arg Val Ser Phe Phe Ala Trp His Arg Ala
            260                 265                 270

CTC AGC CCG GAG TCC GGC GCC CAG CCT AGT GCG GCA TCC CAT CCA CTT    864
Leu Ser Pro Glu Ser Gly Ala Gln Pro Ser Ala Ala Ser His Pro Leu
            275                 280                 285

AGC CCG GAT CAG CCC AAT GGC GGC ATC CTG GAG AAC TGC GTG GCC CAG    912
Ser Pro Asp Gln Pro Asn Gly Gly Ile Leu Glu Asn Cys Val Ala Gln
            290                 295                 300

GCC TCA GAC GAC GGC TCC TGG TGG GAC CAT GAC TGT GAG CGG CGC CTC    960
Ala Ser Asp Asp Gly Ser Trp Trp Asp His Asp Cys Glu Arg Arg Leu
305                 310                 315                 320

TAC TTC GTC TGC GAG TTC CCT TTC                                    984
Tyr Phe Val Cys Glu Phe Pro Phe
                325
```

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:14:

```
ATTTGGGTGC TGGGAAGCCC AGCT                                         24
```

(2) INFORMATION FOR SEQ ID NO:15:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:15:

TCCTGGGCAG AGACCGGTTC TCTA                                          24

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Ala Arg Gly Ala Glu Arg Glu Xaa Glu Gly
1               5                   10

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "acetylarginine"

(xi) SEQUENCE DESCRIPTION: SEQ ID NO:17:

Xaa Glu Trp Glu Gly Gly Trp Gly Gly Ala Gln Glu Glu Glu Arg Glu
1               5                   10                  15

Arg Glu Ala Leu Cys
            20

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GAGACTCGAG TTTT                                                     14

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AAAACTCGAG TCTC                                                14

(2) INFORMATION FOR SEQ ID NO:20:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AATTCGGCAC GAG                                                 13

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AATTCGGCAC GAGAAAACTC GAGTCTCCTC GTGCCG                        36

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AATTCGGCAC GAGAAAAC                                            18

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..36

(xi) SEQUENCE DESCRIPTION: SEQ ID NO:23:

CTG GTT CCG GGT GGA TCC CCG GGA ATT CAT CGT GAC TGACTGACG      45
Leu Val Pro Gly Gly Ser Pro Gly Ile His Arg Asp
  1               5                  10

(2) INFORMATION FOR SEQ ID NO:24:

(i) SEQUENCE CHARACTERISTICS:
        (A) LENGTH: 12 amino acids
        (B) TYPE: amino acid
        (D) TOPOLOGY: linear

```
        (ii) MOLECULE TYPE: protein (xi) SEQUENCE DESCRIPTION: SEQ ID NO:24:

Leu Val Pro Gly Gly Ser Pro Gly Ile His Arg Asp
 1               5                   10

(2) INFORMATION FOR SEQ ID NO:25:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: CDS
            (B) LOCATION: 1..30

(xi) SEQUENCE DESCRIPTION: SEQ ID NO:25:

CTG GTT CCG CGT GGA TCC GGC CAT GGG GCT TCTAGAATTC            40
Leu Val Pro Arg Gly Ser Gly His Gly Ala
 1               5                   10

(2) INFORMATION FOR SEQ ID NO:26:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO:26:

Leu Val Pro Arg Gly Ser Gly His Gly Ala
 1               5                   10
```